(12) United States Patent
Andersson et al.

(10) Patent No.: US 6,919,058 B2
(45) Date of Patent: Jul. 19, 2005

(54) RETAINING MICROFLUIDIC MICROCAVITY AND OTHER MICROFLUIDIC STRUCTURES

(75) Inventors: Per Andersson, Uppsala (SE); Gunnar Ekstrand, Uppsala (SE)

(73) Assignee: Gyros AB, Uppsala (SE)

( * ) Notice: Subject to any disclaimer, the term of this patent is extended or adjusted under 35 U.S.C. 154(b) by 134 days.

(21) Appl. No.: 10/229,676

(22) Filed: Aug. 28, 2002

(65) Prior Publication Data

US 2003/0044322 A1 Mar. 6, 2003

Related U.S. Application Data

(60) Provisional application No. 60/315,471, filed on Aug. 28, 2001, provisional application No. 60/322,621, filed on Sep. 17, 2001, and provisional application No. 60/376,776, filed on Apr. 30, 2002.

(30) Foreign Application Priority Data

| Oct. 21, 2001 | (SE) | 0103522 |
|---|---|---|
| Dec. 5, 2001 | (SE) | 0104077 |
| Mar. 19, 2002 | (WO) | PCT/SE02/00531 |
| Mar. 19, 2002 | (WO) | PCT/SE02/00537 |
| Mar. 19, 2002 | (WO) | PCT/SE02/00538 |
| Mar. 19, 2002 | (WO) | PCT/SE02/00539 |
| Apr. 30, 2002 | (SE) | 0201310 |

(51) Int. Cl.[7] .............................................. B01F 15/02
(52) U.S. Cl. ........................................ 422/341; 422/100
(58) Field of Search ........................... 366/341, DIG. 4; 422/99, 100

(56) References Cited

U.S. PATENT DOCUMENTS

| 4,233,029 A | 11/1980 | Columbus |
|---|---|---|
| 4,254,083 A | 3/1981 | Columbus |
| 4,279,862 A | 7/1981 | Bretaudiere et al. |
| 5,160,702 A | 11/1992 | Kopf-Sill et al. |
| 5,472,603 A | 12/1995 | Schembri |
| 5,637,469 A | 6/1997 | Wilding et al. |
| 6,063,589 A | 5/2000 | Kellogg et al. |
| 6,117,396 A | 9/2000 | Demers |
| 6,143,247 A | 11/2000 | Sheppard, Jr. et al. |

FOREIGN PATENT DOCUMENTS

| EP | 0 528 472 A2 | 2/1993 |
|---|---|---|
| WO | 95/06870 A1 | 3/1995 |
| WO | 95/33986 A2 | 12/1995 |

(Continued)

OTHER PUBLICATIONS

Microfluidics in a Rotating CD; Presented at MICROTAS 2000, Enschede, The Netherlands, May 14–18, 2000.
High–Throughput SNP Scoring in a Disposable Microfabricated CD Device; Presented at HGM 2000, Vancover, Canada, Apr. 9–12, 2000.
PCT International Preliminary Examination Report Nov. 14, 2003.

Primary Examiner—Tony G. Soohoo
(74) Attorney, Agent, or Firm—Fulbright & Jaworski, LLP

(57) ABSTRACT

A microfluidic device that comprises several microchannel structures in which there are an inlet port, an outlet port and there between a structural unit comprising a fluidic function. The structural unit can be selected amongst units enabling a) retaining of nl-aliquots comprising constituents which has been defined by mixing of aliquots within the microfluidic device (unit A), b) mixing of aliquots of liquids (unit B), c) partition of larger aliquots of liquids into smaller aliquots of liquids and distributing the latter individually and in parallel to different microchannel structure of the same microfluidic device (unit C), d) quick penetration into a microchannel structure of an aliquot of a liquid dispensed to an inlet port of a microchannel structure (unit D), and e) volume definition integrated within a microchannel structure (unit E).

17 Claims, 11 Drawing Sheets

FOREIGN PATENT DOCUMENTS

| | | | |
|---|---|---|---|
| WO | 97/21090 | A1 | 6/1997 |
| WO | 98/07019 | A1 | 2/1998 |
| WO | 98/53311 | A2 | 11/1998 |
| WO | 99/55827 | A1 | 11/1999 |
| WO | 99/58245 | A1 | 11/1999 |
| WO | 00/25921 | A1 | 5/2000 |
| WO | 00/40750 | A1 | 7/2000 |
| WO | 00/56808 | A2 | 9/2000 |
| WO | 00/62042 | A1 | 10/2000 |
| WO | 00/69560 | A1 | 11/2000 |
| WO | 01/46465 | A2 | 6/2001 |
| WO | 01/46465 | A3 | 6/2001 |
| WO | 01/47637 | A1 | 7/2001 |
| WO | 01/47638 | A2 | 7/2001 |
| WO | 01/54810 | A1 | 8/2001 |
| WO | 01/87485 | A2 | 11/2001 |
| WO | 01/87486 | A2 | 11/2001 |
| WO | 01/87487 | A2 | 11/2001 |
| WO | 02/41997 | A1 | 5/2002 |
| WO | 02/41998 | A1 | 5/2002 |
| WO | 02/074438 | A2 | 9/2002 |
| WO | 02/075312 | A1 | 9/2002 |
| WO | 02/075775 | A1 | 9/2002 |
| WO | 02/075776 | A1 | 9/2002 |
| WO | 02/083310 | A2 | 10/2002 |

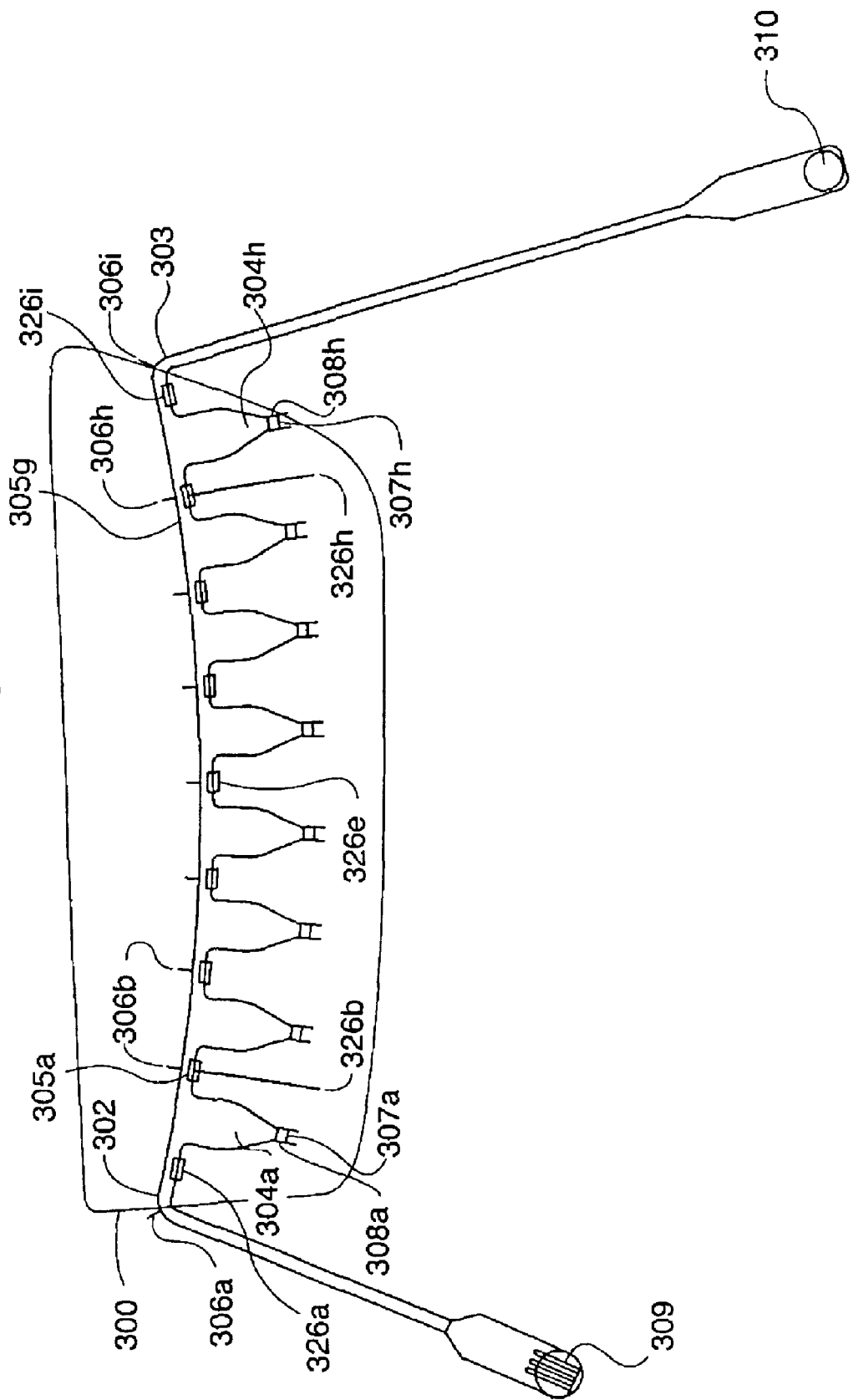

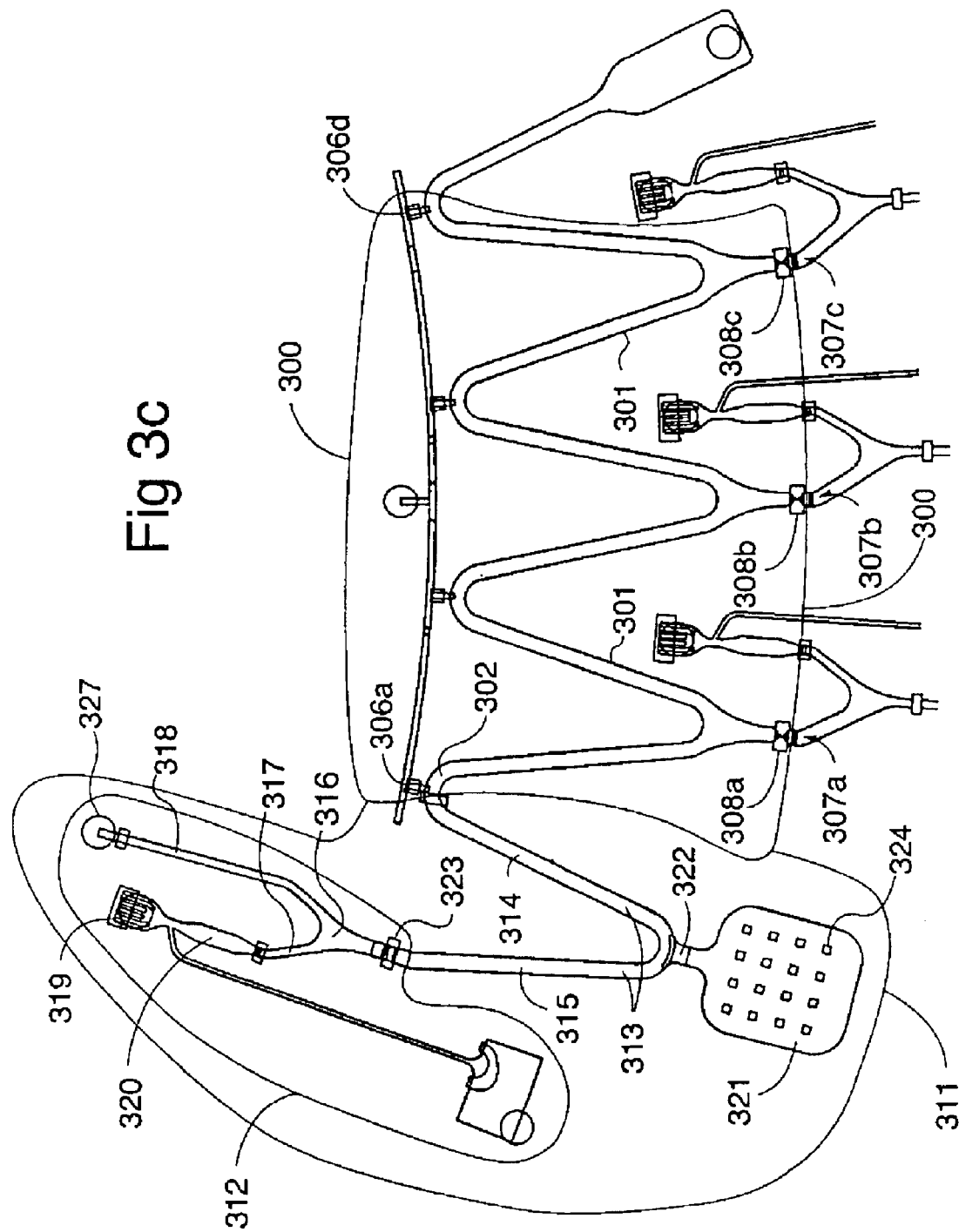

RETAINING MICROFLUIDIC MICROCAVITY AND OTHER MICROFLUIDIC STRUCTURES

The present invention claims priority to U.S. Provisional Application No. 60/315,471, which was filed on Aug. 28, 2001; U.S. Provisional Application No. 60/322,621, which was filed on Sep. 17, 2001; U.S. Provisional Application No. 60/376,776, which was filed on Apr. 30, 2002; International Application PCT/SE02/00531, which was filed on Mar. 19, 2002; International Application PCT/SE02/00537, which was filed on Mar. 19, 2002; U.S. Application No. 10/148,083, which is the National Stage of International Application PCT/SE02/00538 filed on Mar. 19, 2002; and U.S. Application No. 10/148,084, which is the National Stage of International Application PCT/SE02/00539 filed on Mar. 19, 2002, and is a continuation-in-part of U.S. Application No. 10/004,424 filed on Dec. 6, 2001, Swedish Application Nos. 0104077-3 filed Dec. 5, 2001, 0103522-9 filed on Oct. 21, 2001, and 0201310-0 filed Apr. 30, 2002 which are all incorporated herein by reference.

BACKGROUND OF THE INVENTION

I. Field of Invention

The present invention concerns a microfluidic device in which there is a microchannel structure which comprises (a) one or more inlet ports, (b) one or more outlet ports, and (c) a structural unit which comprises a fluidic function and is located between one of the inlet ports and one of the outlet ports. The structural unit (c) may include an inlet or an outlet port.

According to the invention the structural unit is selected by certain innovative structures permitting a) retaining nl-aliquots of liquids in which the constituents have been defined by mixing of aliquots within the microfluidic device (unit A), b) mixing of aliquots of liquids (unit B), c) partition of larger aliquots of liquids into smaller aliquots of liquids and distributing the latter individually and in parallel to different microchannel structure of the same microfluidic device (unit C), d) quick penetration into a microchannel structure of an aliquot of a liquid dispensed to an inlet port of a microchannel structures (unit D), and e) volume definition integrated within a microchannel structure (unit E). There may in addition also be other structural units and/or microfluidic functionalities included.

II. Related Art

Microfluidic structures have been considered promising for assays, chemical synthesis etc. which are to be performed with a high degree of parallelity. A generally expressed desire has been to run the complete sequence of steps of test protocols, including sample treatment within microfluidic devices. This has lead to a desire to dense-pack microchannel structures on planar substrates (chips) and to integrate valve functions, separation functions, means for moving liquids etc. within microfluidic devices. In the macroscopic world these kinds of functionalities can easily be integrated into various kinds of liquid transportation systems, but in the microscopic world it has become expensive, unreliable etc. to miniaturize the macroscopic designs. The situation becomes still worse when moving from $\mu$l- to nl-aliquots or from microchannel dimensions of above 100 $\mu$m down to those less than 100 $\mu$m. One of the main reasons for this is that the surface forces of liquids are more influential on liquid behavior when going down in volume from the $\mu$l-volumes to the nl volumes and smaller, for instance when going below 5 $\mu$l. A typically example is that wicking/imbibing will promote quick liquid transport from a nl-vessel making it difficult to retain a specified liquid volume in such a vessel.

I. Centrifugal Force for Moving Liquids in Microfluidic Devices

The use of centrifugal force for moving liquids within microfluidic systems has been described for instance by Abaxis Inc (WO 9533986, WO 9506870, U.S. Pat. No. 5,472,603); Molecular devices (U.S. Pat. No. 5,160,702); Gamera Biosciences/Tecan (WO 9721090, WO 9807019, WO 9853311), WO 01877486, WO 0187487; Gyros AB/Amersham Pharmacia Biotech (WO 9955827, WO 9958245, WO 0025921, WO 0040750, WO 0056808, WO 0062042, WO 0102737, WO 0146465, WO 0147637, WO 0147638, WO 0154810, WO 0241997, WO 0241998, WO 2002074438, WO 2002075312, WO 200275775, WO 2002075776). See also presentations made by Gyros AB at various scientific meetings: (1) High-through put screening SNP scoring in microfabricated device. Nigel Tooke (September 99); (2) Microfluidics in a rotating CD (Ekstrand et al) MicroTAS 2000, Enschede, The Netherlands, May 14–18, 2000. (3)(a) SNP scoring in a disposable microfabricated CD device (Eckersten et al) and (b) SNP scoring in a disposable microfabricated CD device combined with solid phase Pyrosequencing™ (Tooke et al) Human Genome Meeting, HGM 2000, Vancouver, Canada, Apr. 9–12, 2000, (4) Integrated sample preparation and MALDI MS on a microfluidic compact disc (CD with improved sensitivity (Magnus Gustavsson et al) ASMS 2001 (spring 2001).

II. Unit A: Retaining Microcavity for nl-aliquots

The proprietor of the present invention has during the last year developed microfluidic systems comprising structural units comprising microcavities intended for nl-volumes of liquids. See for instance WO 9955827, WO 9958245; WO 0040750, WO 0146465, WO 0147638, WO 0241997, and WO 0241997 and scientific presentations made by Gyros AB (see above). Hydrophobic surface breaks for preventing undesired creeping of liquid around corners or as valves have in particular been emphasized in WO 9958245. See also WO 2002074438, WO 2002075312, WO 2002075775 and WO 2002075776.

III. Unit B: Mixing Unit

Units for mixing aliquots within microfluidic devices have previously been described. These units have been based on (a) mechanical mixers in mixing microcavities or microconduits including creation of turbulence by fixed streric hinders (e.g., WO 9721090 and U.S. Pat. No. 4,279,862 (Bretaudiere et al)); (b) creation of turbulent flow in a microcavity by two incoming liquid flows (e.g., WO 9853311); (c) creation of a laminar flow in the inlet end of a mixing microconduit and achieving mixing by diffusion during the transport through the microconduit (e.g., U.S. Pat. No. 5,637,469, (Wilding & Kricka); (d) mixing by pumping layered aliquots back and forth in a mixing microcavity or microconduit. This can be accomplished by applying pulsed centrifugal force by spin pulses that drive the liquid in one direction and a higher spin pulse and in the reverse direction at a lower spin pulse utilizing energy built up in the system during a high pulse for driving the liquid in the reverse direction during a lower spin pulses. This can be accomplished by utilizing enclosed air ballast chambers and/or hydrophobic/hydrophilic as outlined in WO 0187487. The principle of back and forth transport is also described in WO 2002074438 (unit 5) and WO 9958245.

IV. Unit C: Distribution Manifold

According to the inventors knowledge publications related to this topic are rare. U.S. Pat. No. 6,117,396

(Orchid) gives a non-centrifugal gravity based microfluidic device in which a common reagent channel is used both as an overflow channel and as a reagent fill channel. A plurality of parallel volume metering capillaries is connected at different positions to the reagent fill channel from below. A centrifugally based distribution manifold for microfluidic systems has been given in WO 9958245 and WO 0187486. This latter variant is based on an annular distribution microconduit and comprises at least one waste/overflow microconduit per aliquot to be dispensed.

Microfluidic devices with a microchannel structures that comprises a part that bents towards a lower level (downward bent) and/or a part that bents towards a higher level (upward bent) have been described previously. Downward and upward bents have been linked to each other in short series. Bent structures for centrifugal based system have been used for metering liquids, process chambers etc.

Downward bents have been combined with centrifugal force and used for retaining liquid (valve function) that is to be subjected to distinct process steps in the bent, e.g., chemical or biochemical reactions, affinity reactions, measurement operations, volume metering etc. By including an outlet microconduit with a valve function, for instance a passive valve, in the lower part of the bent, processed aliquots can been transported further downstream in the structure in a controlled manner.

Further details about previously known bent structure are given in: WO 9958245; WO 0147638; WO 0146465; WO 0040750; WO 2002074438, WO 2002075312, WO 2002075775 and WO 2002075776; WO 0241997 and WO 0241998. Bent structures have also been indicated in scientific presentations made by Gyros AB and given elsewhere in this specification.

V. Unit D: Inlet Port

Imbibing has been utilized to promote liquid penetration into microchannel structures by including edge/corner structures associated with inlet ports. See U.S. Pat. No. 4,233,029 (Eastman Kodak) and U.S. Pat. No. 4,254,083 (Eastman Kodak).

VI. Unit E: Integrated Volume-Defining Unit

Integrated volume defining units in microfluidic systems are previously known. U.S. Pat. No. 6,117,396 (Orchid), for instance, gives a non-centrifugal gravity based system in which a common reagent channel may act as an overflow/filling channel along which there is spaced a plurality of volume metering capillaries for $\mu$l-volumes. Integrated units for metering volumes in centrifugal based system by the use of an overflow channel have been described in WO 9853311, WO 0146465 and WO 0040750.

The present invention is the first to provide novel fluidic functionalities that are used when transporting and processing nl-volumes of liquids in microchannel systems, which are defined herein.

BRIEF SUMMARY OF THE INVENTION

The microchannel structures of the present invention are intended for transport and processing of one or more aliquots of liquids (thus the device is named microfluidic). In preferred variants capillary force and centrifugal force are used for the transport of the aliquots. The invention also concerns various methods in which the microfluidic device/microchannel structures is/are used.

In one first aspect, the invention relates to the microfluidic device as generally defined herein. A characteristic feature of this aspect of the invention is that at least one of the structural units is selected amongst the innovative units A–E described below. Units that combine the functionality and/or structure of two or more of the units A–E may be included. Other units that are known or will be known in the future may also be included as long as at least one of the innovative units A–E is present. For additional units see also PCT/SE02/00531.

In preferred variants of this aspect at least one of the aliquots referred to in the description of a structural unit should have a surface tension, which is $\geq 5$ mN/m, such as $\geq 10$ mN/m or $\geq 20$ mN/m.

A second aspect of the invention is a method for transporting one, two or more aliquots through a microchannel structure of the microfluidic device. The method comprises the steps of (i) providing the microfluidic device, (ii) providing said one, two or more aliquots, (iii) introducing each of said aliquots through an inlet port of one, two or more microchannel structures of the device, (iv) transporting the aliquots through at least one of the structural units which is present between an inlet port and an outlet port without utilizing valves and pumps containing movable mechanical parts, and (v) possibly collecting the aliquots in treated form in one or more of the outlet ports of the microchannel structure. Preferable aspects include that one, two, three or more of the aliquots that are to be introduced through an inlet port of the microchannel structures have a surface tension which is $\geq 5$ mN/m, such as $\geq 10$ mN/m or $\geq 20$ mN/m.

The microfluidic device provided in step (i) is according to the first aspect. In step (ii), at least one of the aliquots has a volume in the nano-litre range. In step (iii) two or more of the aliquots may be introduced via the same or different inlet ports. In step (iv) the driving force utilized for transport of the aliquots typically is capillary force and/or inertia force without excluding other kinds of forces as discussed elsewhere in this specification.

Steps (iii) and (iv) include that the various aliquots are processed according to an intended protocol, i.e., the transport step (step (iv)) includes that an aliquot introduced into a microchannel structure may be transported to a certain position (structural unit) and/or processed in a predetermined manner before the next aliquot is introduced. The part sequence that comprises steps (iii) and (iv) may thus be interrupted for dispensation steps, process steps etc. to take place, be divided in substeps. For instance, The two reactants may be dispensed separately in sequence to the same or to different inlet ports and then mixed in a separate mixing unit as discussed elsewhere in this specification. Subsequent to the mixing the reaction mixture is transported to a reaction microcavity and retained therein while the reaction is allowed to proceed according to the desired protocol, after which the result of the reaction is analyzed in the same microcavity or further downstream or outside the microchannel structure. The analysis may involve determination/detection of products and/or the disappearance of one or more of the reactants. By properly designing the system the proceeding of the reactions may be followed through the wall of the microcavity, i.e., there may also be substeps run in parallel (measuring and incubation).

In step (v) the term "treated form" contemplates that the aliquots have passed the structure and been subjected to one or more predetermined treatments. The chemical composition may have changed and/or aliquots may have been mixed.

At least one of the aliquots is typically aqueous and/or may contain one or more surface-active agents that increase or decrease the surface tension of a liquid, such as water. Typical agents that reduce surface tension are detergents that may be cationic, anionic, amphoteric or non-ionizable. Surface-active agents include organic solvents, preferably miscible with water. Examples are methanol, ethanol, isopropanol, formamide, acetonitrile etc. Charged or chargeable polymers, biomolecules such as proteins, certain sugars etc. may also act as surface-active agents.

The foregoing has outlined rather broadly the features and technical advantages of the present invention in order that the detailed description of the invention that follows may be better understood. Additional features and advantages of the invention will be described hereinafter which form the subject of the claims of the invention. It should be appreciated by those skilled in the art that the conception and specific embodiment disclosed may be readily utilized as a basis for modifying or designing other structures for carrying out the same purposes of the present invention. It should also be realized by those skilled in the art that such equivalent constructions do not depart from the spirit and scope of the invention as set forth in the appended claims. The novel features which are believed to be characteristic of the invention, both as to its organization and method of operation, together with further objects and advantages will be better understood from the following description when considered in connection with the accompanying figures. It is to be expressly understood, however, that each of the figures is provided for the purpose of illustration and description only and is not intended as a definition of the limits of the present invention.

BRIEF DESCRIPTION OF THE DRAWINGS

For a more complete understanding of the present invention, reference is now made to the following descriptions taken in conjunction with the accompanying drawing, in which:

FIG. 3A–FIG. 3C illustrate innovative variants of unit C;

The structural units are viewed from above. The cross-sectional areas of the microconduits and microcavities are typically rectangular. The depths of the microchannel structures shown are typically constant and within the interval 100–150 $\mu$m. The widths for liquid transport microconduits are typically within the interval 100–300 $\mu$m and for air microconduits within the interval of 40–100 $\mu$m. Also compare the figures in WO 2002074438, WO 2002075312, WO 2002075775, WO 2002075776 (all of Gyros AB), which disclose other structures of comparable dimensions. FIGS. 2c–d specifically include certain dimensions in $\mu$m. Circles represent openings to ambient atmospheres (inlet port, outlet ports, vents etc.).

DETAILED DESCRIPTION OF THE INVENTION

Figure 1:
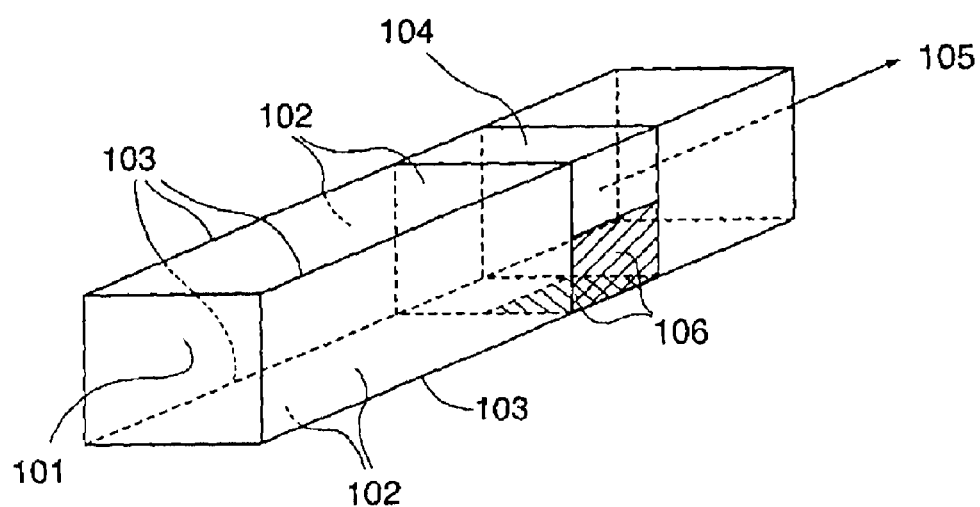
FIG. 1 illustrates the definitions of "edge" and "circumferential zone"

The present invention provides novel fluidic functionalities that can be used when transporting and processing nl-volumes of liquids in microchannel systems of the kind defined herein. A particular intention is to create functionalities that do not require movable mechanical parts, e.g., to accomplish valving, pumping, mixing etc., and can be integrated into the microchannels and/or the substrates. The various novel functionalities are based on local surface characteristics of the inner walls of the microchannels and/or on properties of the liquids, such as surface tension and wetting ability.

A first object is to provide a structural unit with a functionality that permits retaining of a defined nl-aliquot for prolonged period of time in a predetermined microcavity (retaining microcavity) of a microchannel structure of a microfluidic device. The nl-aliquots concerned are obtained by mixing nl-aliquots within the microchannel structure. Yet further, the term "aliquot" refers to an aliquot of a liquid if not otherwise specified. The term "prolonged" typically means that the liquid is retained in the retaining microcavity under static conditions, i.e., non-flow conditions. The period of time concerned is typically $\geq 15$ seconds, such as 30 seconds or $\geq 1$ minute, such as $\geq 5$ minutes or $\geq 10$ minutes, for instance $\geq 1$ hours or $\geq 10$ hours. The contemplated periods last typically $\leq 24$ hours such as $\leq 12$ hours. This object primarily aims at minimizing liquid losses due to wicking and/or evaporation from retaining microcavities with volumes in the nl-range during incubations for performing reactions and measurements in the mixed nl-aliquot, for storage purposes etc. Acceptable losses are typically $\leq 20\%$, such as $\leq 10\%$ or $\leq 5\%$.

A second object is to provide a structural unit with a functionality that permits simple, quick, safe, reproducible and reliable mixing of two aliquots that are miscible with each other within a microchannel structure of a microfluidic device.

A third object is to provide a structural unit with a functionality that permits simplified and reliable distribution in parallel to separate substructures of a plurality of microchannel structures in a microfluidic device.

A fourth object is to provide a structural unit with a functionality that facilitates rapid introduction of an aliquot into a microchannel structure of a microfluidic device.

A fifth object is to provide a structural unit with a functionality that enables reproducibly metering of an aliquot within a microchannel structure before the aliquot is transported further downstream in a microchannel structure of a microfluidic device.

Subobjects related to the above-mentioned objects correspond to methods and uses of the microfluidic devices/structural units for transporting and processing the aliquots of liquids. A particular subobject to the first object is a method for reducing evaporation caused by wicking from the type of nl-aliquot referred to.

The invention is among others based on the recognition that the appropriate surface tension of a liquid is important for controlling a liquid flow in a microsystem. This in particular applies when dealing with aliquots in the nano-litre range and/or if the control is exerted without mechanical valves and pumps, i.e., by driving the transport of aliquots through a functional unit of the invention by capillary force and/or inertia force etc. Typical examples of inertia force are gravitational force and centrifugal force. See also under the heading "Means for driving the liquid flow".

I. Microfluidic Devices

The microfluidic device of the present invention typically comprises one, two, three, four or more sets of microchannel structures in which aliquots are transported or processed for various purposes, for instance analytical or synthetic purposes. The prefix "micro" contemplates that an individual microchannel structure comprises one or more cavities and/or channels that have a depth and/or a width that is $\leq 10^3 \mu$m, such as $\leq 10^2 \mu$m. The lower limit for the width/breadth is typically significantly larger than the size of the largest reagents and constituents of aliquots that are to pass through a microchannel. The volumes of microcavities and thus also of aliquots to be transported and processed are typically $\leq 1000$ nl, such as $\leq 500$ nl or $\leq 100$ nl or $\leq 50$ nl. The nl-range comprises, if not otherwise specified, volumes <5000 nl, e.g., within the ranges specified in the preceding sentence. There may also be larger cavities, e.g., directly connected to inlet ports, with a volume within intervals, such as 1–10 $\mu$l, 1–100 $\mu$l, and 1–1000 $\mu$l ($\mu$l-range). These cavities are typically used for the introduction of samples that are to be concentrated within a microchannel structure, or of washing liquids and the like.

The term "microconduit" means a part of a microchannel structure.

A microconduit may be intended for transport of liquids (liquid flow microconduits) or for transport into or out of the microchannel structure (air microconduits). The dimensions of the two types may be different, for instance an air microconduit may have a smaller cross-sectional area and/or a higher aspect ratio (depth:width) compared to a liquid flow microconduit or vice versa. The liquid flow microconduit thus may have an aspect ratio $\leq 1$ while an air microconduit may have an aspect ratio $\geq 1$ or vice versa, or the aspect ratio may be equal for the microconduit irrespective of their use. A liquid flow channel typically has hydrophilic inner surfaces as discussed elsewhere in this specification while an air channel typically has hydrophobic inner surfaces. Liquid flow microconduits may also be used for venting air into or out of a microchannel structure.

The terms "inlet port" and "outlet port" contemplate port for air and ports for liquids.

A microchannel structure may comprise a number of functional units that are necessary to carry out a predetermined protocol within the structure. A microchannel structure thus may comprise one, two, three or more units selected amongst inlet ports, outlet ports, units for distributing samples, liquids and/or reagents to individual microchannel structures, microconduits for liquid transport, units for defining liquid volumes, valving units, units venting to ambient atmosphere, units for mixing liquids, units for performing chemical reactions or bioreactions, units for separating soluble constituents or particulate materials from a liquid phase, waste liquid units including waste cavities and overflow channels, detection units, units for collecting an aliquot processed in the structure and to be transferred to another device e.g., for analysis, branching units for merging or dividing a liquid flow, etc. In one and the same microchannel structure there may be several inlet ports and/or several outlet ports that are connected to a main flow path via microconduits at a different or at the same downstream position. These microconduits may also contain functional units of the type discussed above.

Typically a microfluidic device comprises in total $\geq 50$, such as $\geq 100$ or $\geq 200$, microchannel structures per microfluidic device. The microchannel structures of a set are essentially identical and may or may not extend in a common plane of a substrate. There may be channels providing liquid communication between individual microchannel structures of a set and/or to one or more other sets that may be present in the same device. The microchannels are typically covered, i.e., surrounded by walls or other means for directing the flow and to lower evaporation. Openings such as in inlet ports, outlet ports, vents etc. are typically present where appropriate.

The cross-section of a microchannel may have rounded forms all around, i.e., be circular, ellipsoid etc. A microchannel may also have inner edges, i.e., have cross-sections that are triangular, squaric, rectangular, partly rounded, planar etc. Microcavities or microchambers may have the same or a different cross-sectional geometry compared to surrounding microconduits.

If not otherwise indicated the term "edge" of a microconduit will refer to the intersection of two inner walls of the microconduit. This kind of edges is typically extending more or less in parallel along the flow-direction (length-going edges). See FIG. 1 that shows a microchannel having a rectangular cross-section (101), four inner walls (102) with four wall intersections or edges (103). The arrow (105) gives the flow direction.

A circumferential zone of a microchannel is also illustrated in FIG. 1. It is an inner surface zone (104) in the inner wall of a microchannel and extends in a sleeve-like manner around the flow direction (105). The length of this kind of zone is at least from 0.1–10, 0.1–100, 0.1–1000 or more times the breadth or depth of the microchannel/microconduit at the upstream end of the zone.

The microfluidic device may have an axis of symmetry that is n-numbered ($C_n$) where n is an integer between 2 and $\infty$, preferably 6, 7, 8 and larger, for instance $\infty$. In preferred cases the microfluidic device as such may have a cylindrical, spherical or conical symmetry ($C_\infty$) and/or is disc-shaped. Axes of symmetry may be combined with utilizing centrifugal force created by spinning around the axis of symmetry for driving a liquid flow through a microchannel structure.

The microfluidic device is typically in the form of a disc with the microchannel structures extending in a plane parallel to the disc plane.

The devices can be manufactured as summarized in WO 2002074438.

The devices are preferably of the same dimension as a conventional CD, but may also be smaller, for instance down to 10% of conventional CDs, or larger, for instance up to more than 200% or more than 400% of a conventional CD. These percentage values refer to the radius.

In the preferred variants the microchannel structures comprises inner surfaces that have been hydrophilized, for instance as described in WO 0056808. If necessary the inner surfaces may be coated with a non-ionic hydrophilic polymer as described in WO 0056808 or and U.S. Pat. No. 5,773,488 (Gyros AB), for instance. The preferred variants are the same as given in these publications, e.g., to a wettability allowing for capillarity to draw a liquid into a structural unit once having passed the inlet thereof. Where appropriate hydrophobic surface breaks are introduced as outlined in WO 9958245 and WO 2002074438. See also WO 0185602 (Åmic AB & Gyros AB), which are incorporated herein by reference.

The exact demand on liquid contact angles (hydrophilicity/hydrophobicity) of inner surfaces of the microchannel structure may vary between different functional units. Except for local hydrophobic surface breaks the liquid contact angel for at least two or three inner walls of a microconduit at a particular location should be wettable (hydrophilic) for the liquid to be transported, with preference for liquid contact angles that are $\leq 60°$, such as $\leq 50°$ or $\leq 40°$ or $\leq 30°$ or $\leq 20°$. In the case one or more walls have higher liquid contact angles, for instance non-wettable (hydrophobic), this can be compensated by a lowered liquid contact angle on the remaining walls. This may be particular important if non-wettable lids are used to cover open hydrophilic microchannel structures. The values above apply for the liquid to be transported and to the functional units given above (except for local hydrophobic surface breaks) and at the temperature of use. Surfaces having water contact angles within the limits given above may often be used for other aqueous liquids.

The terms "wettable surface" and "hydrophilic surface" are mostly contemplated a surface that has a liquid contact angle of $\leq 90°$ (in particular for water and other aqueous media). Surfaces that are "non-wettable" or "hydrophobic" thus typically have a liquid contact angle $\geq 90°$. The liquid contact angle in the normal case refers to equilibrium contact angles although it sometimes may refer to receding and/or advancing contact angles depending on the purpose of a measurement. In the context of the invention equilibrium contact angles are primarily contemplated.

A. Valve Functions

Three categories of valves that previously have been suggested for microfluidic devices are: 1) mechanical valves; 2) valves that comprise intersecting channels together with means that determine through which channel a liquid flow shall be created; 3) inner valves, i.e., valves in which the passage or non-passage of a liquid depends on physical and/or chemical properties of the liquid and the material in the surface of the inner wall of a microconduit at the position of an inner valve.

Type 1 valves typically require physically closing of a microconduit are therefore called "closing valves". They often have movable mechanical parts for closing a microconduit.

Type 2 valves function without closing and are therefore "non-closing". A typical example is directing an electrokinetic flow at the intersection of two channels by switching the electrodes. See for instance U.S. Pat. No. 5,716,825 (Hewlett Packard) and U.S. Pat. No. 5,705,813 (Hewlett Packard).

In type 3 valves, the non-passage or passage of a liquid may be based on: (a) changing the cross-sectional area in a microconduit at the valve position by changing the energy input to the material of the wall in the microconduit (closing valves), and/or (b) locally changing the interaction energy between a through-flowing aliquot and an inner surface of a microconduit at the valve position (non-closing valves), and/or (c) a suitable curvature of the microconduit at the valve function (geometric valves, non-closing).

Type 3a valves are illustrated in WO 0102737 (Gyros AB) in which stimulus-responsive polymers (intelligent polymers) are suggested to create a valve function, and in WO 9721090 in which relaxation of non-equilibrium polymeric structures and meltable wax plugs are suggested to create a valve function.

In type 3b valves, the microconduit at the position of the valve is open even if the liquid is stopped (inner valves including capillary valves, also called passive valves). Through flow in this kind of valves is accomplished simply by increasing the force driving the liquid. The use of hydrophobic surface breaks (changes in chemical surface characteristics) as valves is described in for instance WO 9958245, WO 0146465, WO 0185602 (Åmic AB & Gyros AB), WO 0187486 and WO 2002074438. The use of changes in geometric surface characteristics as valves is described in for instance WO 9615576 (David Sarnoff Res. Inst.), EP 305210 (Biotrack), and WO 9807019. Type 3b valves comprise an anti-wicking function if they utilize changes in chemical and/or geometrical surface characteristics in edges as described for anti-wicking means.

Type 3c valves may be achieved by linking an upward bent of a microchannel immediately downstream to a downward bent in centrifugal based systems. This is illustrated in WO 0146465 that suggests connecting an upward bent microconduit downstream to a U/Y-shaped microconduit.

B. Anti-Wicking Means

Anti-wicking means are typically local surface modifications that counteract wicking/imbibing.

Imbibing (wicking) means that liquid transport is initiated in the edges of micro channels. See for instance Dong et al (J. Coll. Interface Science 172 (1995) 278–288) and Kim et al (J. Phys. Chem. B 101 (1997) 855–863). Imbibing renders it difficult to retain a defined volume of a liquid in a desired microcavity for a longer period of time in case there is a microconduit having a length-going edge directly connected to the microcavity. This in particular applies if the volume $\leq 5$ $\mu$l, such as in the nl-range or less. If the microconduit is connected to ambient atmosphere, for instance via an inlet port, imbibing will promote evaporation and irreversible loss of a predispensed volume of a liquid.

Anti-wicking means typically comprises a change in surface characteristics, such as in geometric and/or chemical surface characteristics, in an inner edge of a microconduit. The edge typically starts in a microcavity and stretches into the microconduit. Anti-wicking means may be present upstream or downstream a microcavity intended to contain a liquid. An anti-wicking functionality may inherently also be present in inner valves that are based on the presence of a hydrophobic surface break in an inner edge.

The change in geometric surface characteristics is typical local and may be selected from indentations, protrusions (projections), and an increase in the angle between the two inner walls defining a length-going inner edge. In most cases the deformation will also stretch into and/or across a wall delineated by this kind of edge, for instance into and/or across a wall delineated by two edges comprising the deformation. For indentations and protrusions this will mean valleys/grooves and ridges, respectively, across the wall. An increase in the angle between two intersecting walls means in its extreme that the inner edge can be rounded within a zone carrying the anti-wicking means but not rounded between this zone and the microcavity. The microconduit thus may locally be cylindrical. Also other physical deformations of the edges may result in anti-wicking.

Deformations in the form of indentations, for instance, may be "ear-like" as illustrated in the figures (214, 406, 509) of the present specification or similar to a triangular groove as illustrated in FIG. 13 (1312) of WO 2002074438, which is incorporated by reference.

A change in chemical surface characteristics (surface break) in the context of anti-wicking primarily refers to a change in hydrophobicity/hydrophilicity of the surface of an inner wall of a microchannel structure. Typically the inner surface of the microconduit is hydrophilic as discussed above with a change into hydrophobicity where anti-wicking is to be achieved.

In a similar manner as for changes in geometric surface characteristics a change in chemical surface characteristics typically may extend into and/or across the inner surface of a wall in a microconduit.

A change in geometric and chemical surface characteristics may fully or partially coincide in the inner surface of microconduit. An indentation and the like which stretches across an inner wall thus physically should comprise the change in chemical surface characteristics if the aim is to avoid valving effects. Compare FIG. 4 (406 and 407).

The anti-wicking means in a circumferential zone that comprise inner edges should be at different positions (or be lacking) in at least one compared to the position of the anti-wicking means in the other edges of the circumferential zone. For instance, if the microconduit has a four-edged cross-section (rectangular) with all four edges extending into a microcavity, opposite inner walls typically may have the change in surface characteristics at different distances, e.g., pair-wise, from the microcavity. Compare for instance FIG. 4.

The anti-wicking means described herein is adapted to prevent wicking for aliquots that have a surface tension, which is $\geq 5$ mN/m, such as $\geq 10$ mN/m or $\geq 20$ mN/m. The importance of including anti-wicking means is primarily related to handling of aliquots $\leq 5$ $\mu$l, such as aliquots in the nl-range, in the microfluidic devices described herein.

Further information about various kinds of anti-wicking means possibly combined with an inner valve function is given in WO 2002074438.

C. Means for Driving the Liquid Flow

The liquid flow may be driven in the microfluidic device of the present invention by distinct means that either is present on a substrate comprising the microchannel structures or is external to the substrate. The former variants typically means liquid flow created by electroendosmosis, by micropumps that are present on the substrate, expanding gas etc. The latter variants typically mean external pressure-generating means that create a liquid flow that is in fluid communication with the microchannel structure. Another alternative is to use forces such as capillary forces and inertia force including gravitational force and centrifugal force. In this latter case no means for moving the liquids is required in the microchannel structures or in the substrates carrying the microchannel structures.

Variants in which the microchannel structures are oriented from an inner position to an outer position in relation to a spinning axis, such as an axis of symmetry of a substrate as described above are typically combined with a spinner that is capable of spinning the substrate around the spinning axis that may coincide with the axis of symmetry. Useful spinners should be able to create the necessary centrifugal force for driving the liquids through at least a part of a microchannel structure. The centrifugal force may be utilized in combination with a second liquid aliquot to create a sufficient local hydrostatic pressure within a structure to drive a first aliquot through an outward (downward) and/or an inward (upward) bent of a microchannel structure. See for instance WO 0146465. Typically spinning speeds are within the interval 50–25000 rpm, such as 50–15000 rpm. The spinning speed within a given protocol may vary and depends on the part structure that is to be passed by a liquid, for instance. In case the microfluidic device contains a plurality of microchannel structures that are to be run in parallel, it may be beneficial to start the passage of liquid through a particular structural unit with a short pulse of increased spinning followed by a slower spinning.

D. Orientations and Positions in a Microfluidic Device

The present invention is primarily intended for geometric arrangements in which the microchannel structure is present in a substrate and arranged about an axis of symmetry (spinning axis) that typically is going through substrate. The term "radial distance" means the shortest distance between an object and the axis of symmetry and/or a spinning axis The radial distance for an inlet port and a structural unit may be the same, or the inlet port may be at a shorter or longer radial distance compared to the structural unit. In a typical case there is also an outlet port for liquid downstream the structural unit, which in most cases is at a larger radial distance than the inlet port. The microchannel structure may or may not be oriented in a plane perpendicular to the axis of symmetry. The terms "higher" and "upper" for a level/position means that an object is at a shorter radial distance (inner position) compared to being at a "lower" level/position (outer position). Similarly, the terms "up", "upward", "inwards", and "down", "downwards", "outwards" etc. will mean towards and from, respectively, the spinning axis. This terminology applies if not otherwise is specified. With respect to other arrangements/substrates and conventional driving forces, i.e., gravity force, externally applied pressure, electro-osmotically (electrokinetically, by electroendoosmosis etc.) driven flows etc., these terms have their conventional meaning.

The terms "downstream" and "upstream" are related to the process protocols and liquid flow as such. The terms thus refer to the order in which a unit, a part, a process step, etc. is utilized. A downstream position is coming after an upstream position.

II. Structural Units A–E

Inlet ports typically have hydrophobized areas to direct applied liquid into the ports. Local surface breaks that are hydrophobic for aqueous liquids are represented by straight or bent rectangles. They are primarily present for controlling liquid flow, e.g., in valves (inner valves), in anti-wicking means, in vents and for directing liquid inwards the structures in inlet ports.

A. Unit A: Retaining Microcavity Unit

The first aspect of the invention is a microfluidic device comprising a microchannel structure in which there is a structural unit accomplishing retaining of a nl-aliquot of liquid in a microcavity (retaining microcavity) as discussed in the first object. The nl-aliquot has been obtained by mixing two liquid aliquots within the microchannel structure and is henceforth named "mixed nl-aliquot" or "mixed aliquot".

The present inventors have recognized that a nl-aliquot placed in a microcavity of a microchannel structure under static non-flow conditions is quickly reduced in volume and may disappear from the microcavity in the case the microchannel structure is openly connected to other parts of the structure, e.g., to inlet ports or outlet ports which directly communicate with ambient atmosphere and to other microcavities not containing liquid. The present inventors have discovered that this effect is related to wicking in inner edges, and that the effect is enhanced if evaporation of a wicked liquid from the outlet and/or inlet ports is possible. The present inventors hereby present a solution to this problem. The solution for a mixed nl-aliquot is to a) place anti-wicking means in the microconduits directly connected to a microcavity intended to retain a well-defined aliquot of liquid, and/or b) secure that the distance within the microchannel structure between the microcavity and each of the outlet ports has a sufficient length.

Figure 2A:
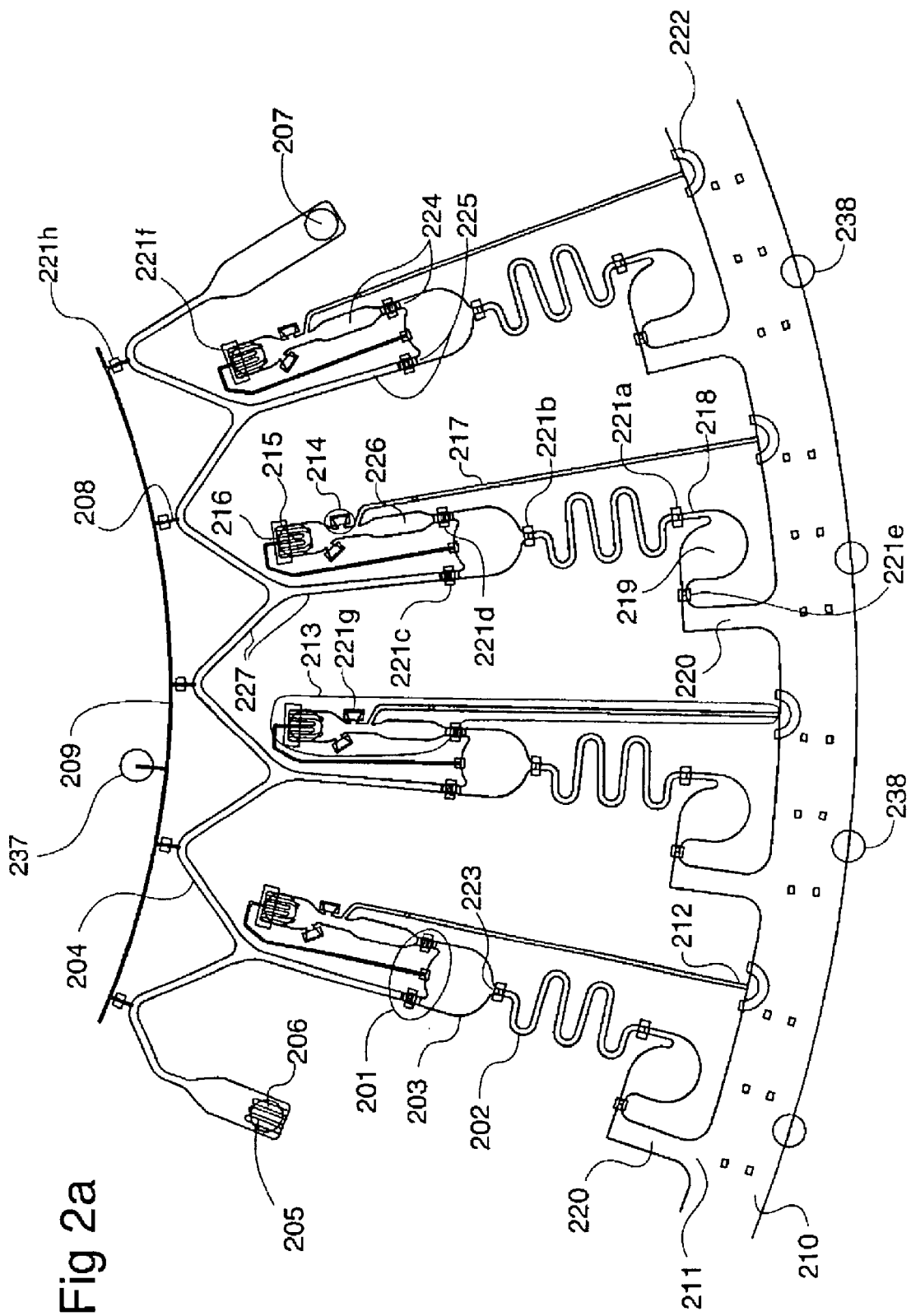
FIG. 2A–FIG. 2e illustrate innovative variants of units A and B.
Figure 2B:
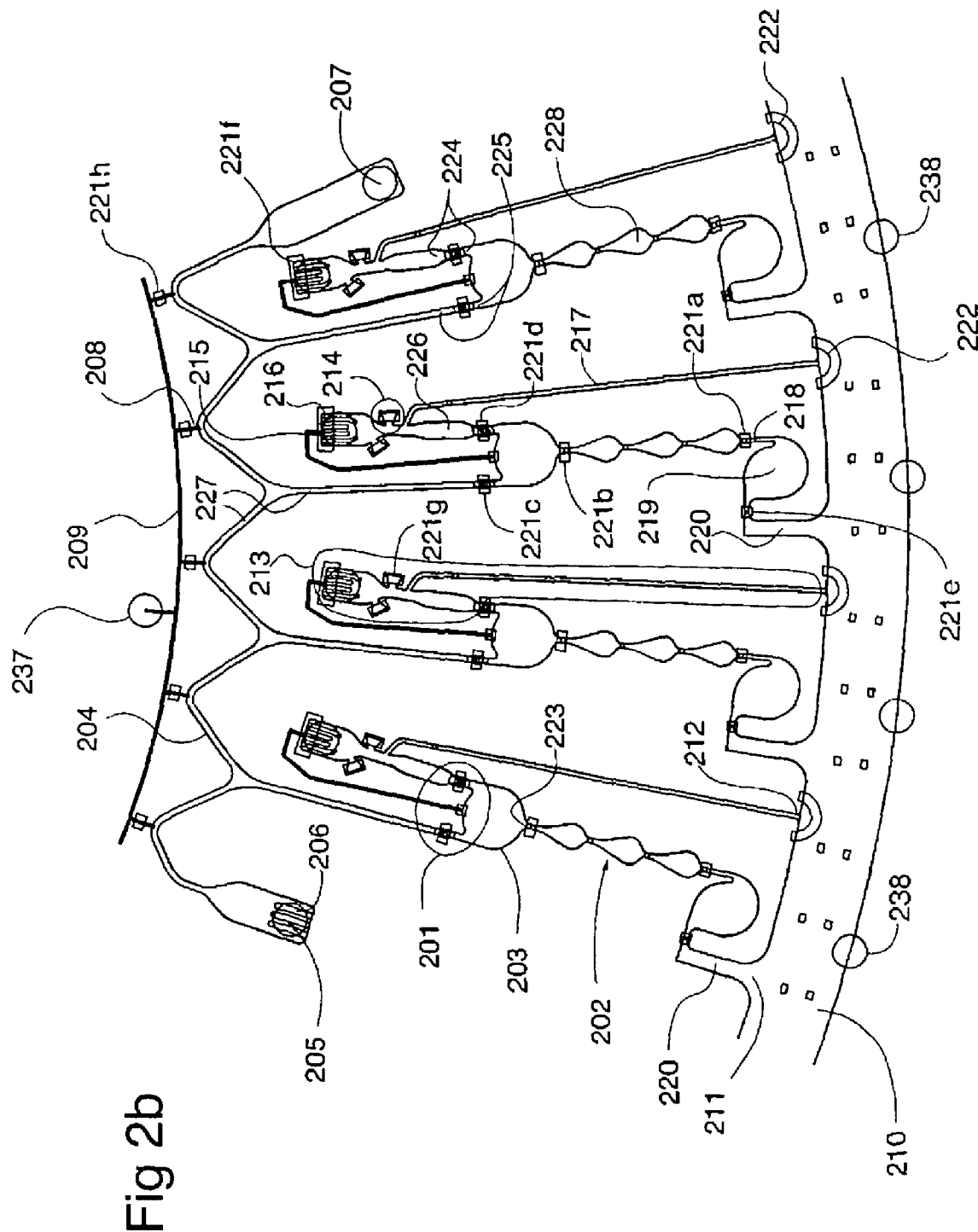

The structural unit of the first aspect of the invention is illustrated in FIGS. 2a–b and d–e. The unit is characterized in comprising (a) a microcavity (retaining microcavity) (219) which is intended for retaining a nl-liquid aliquot (mixed aliquot) under static non-flow conditions and is located between at least one (205,215,237) of said one or more inlet ports (205,215,237) and at least one (238,241) of said one or more outlet ports (207,238,239,240,241); (b) a mixing unit (302+303+301) which is located upstream the retaining microcavity (219) and downstream said at least one inlet port (205,215,237) and in which two or more aliquots (aliquot 1, aliquot 2 etc.) are to be mixed to form said mixed aliquot; and (c) two or more microconduits (218,220,242) directly connected to the retaining microcavity (219) and communicating with one of said inlet or outlet ports (205,207,215,237,238, 239,240,241).

Each of the microconduits (218,220,242) comprises anti-wicking means (221$a,e$) in association with the joint between the retaining microcavity (219) and the microconduit. Alternatively, if a microconduit is directly attached to a retaining microcavity (219) and does not contain anti-wicking means, then the distance ($d_1$) from the retaining microcavity (219) to an opening to ambient atmosphere in an inlet or outlet port (205,207,215,237, 238,239,240,241) is $\geq 10$ times the largest cross-sectional dimension of this microconduit at its joint to the retaining microcavity (219).

The distance ($d_1$) refers to the shortest distance, if alternatives are available. The distance is measured inside the microchannel structure and includes length of the microconduit concerned. The cross-sectional dimension refers to an inner dimension.

The effect of reducing evaporation to ambient atmosphere without anti-wicking means may be further enhanced if the distance ($d_1$) is further increased, e.g., to $\geq 20$ times or $\geq 50$ times or $\geq 100$ times or $\geq 500$ times or $\geq 1000$ times $\geq 5000$ times the largest cross-sectional dimension of this microconduit at its joint to the retaining microcavity (219).

In principle the above-mentioned conditions for microconduits not containing anti-wicking means may be applied to microconduits containing anti-wicking means. Accordingly any microconduit connected to a retaining microcavity (219) may contain both anti-wicking means and comply with the conditions for the distance ($d_1$).

The microconduits connected to the retaining microcavity may be either an air microconduit (242, FIG. 2d) or a liquid flow microconduit (218,220, FIGS. 2a–b and c–d). The latter typically also functions as a microconduit for venting out air displaced by an incoming liquid. Further differences between the two kinds of microconduits are discussed under the heading "Microfluidic device".

One, two or more up to all of the microconduits (218, 220,242) directly connected to the retaining microcavity (219) have one or more length-going edges extending continuously from said retaining microcavity. Each of these edges preferably has anti-wicking means. Air microconduits having hydrophobic inner surfaces at their joint to the retaining microcavity (219) will inherently provide anti-wicking means. See further under the heading "Anti-wicking means".

A liquid flow microconduit (218,220) directly connected to a retaining microcavity (219) typically also comprises a non-closing valve function in association with the joint between the microconduit (218,220) and the microcavity (219). This valve function may be based on a change in geometric and/or chemical surface characteristics and/or on a suitable curvature of these flow microconduits (upward bents) as illustrated in FIGS. 2a–b and e (microconduit 220). The anti-wicking means and the valve functions may fully or partially coincide in a liquid flow microconduit (218,220). See further under the heading "Valve functions".

The mixing unit of the microchannel structure may in principle be any kind of mixing unit that can be adapted to the instant kind of microfluidic structures. This includes the kind of mixing units discussed under the heading "Background publications mixing units (unit B)" and the innovative unit B discussed below. Thus the mixing unit may comprise two inlet microconduits (224 and 225) for the aliquots to be mixed (aliquot 1, aliquot 2). These inlet microconduits merge in the downstream direction into a common microconduit (302) that communicates with the retaining microcavity (219) in the downstream direction. At the intersection of the two inlet microconduits (224 and 225), there may be a microcavity (303) with a total volume that is essentially the same as or larger than the total volume of the aliquots to be mixed and introduced via the inlet microconduits. There may also be further inlet microconduits merging at the intersection or elsewhere for mixing of additional aliquots with aliquot 1 and aliquot 2. Mixing may occur in the common microconduit (302) (mixing microconduit), or in the microcavity (303) (mixing microcavity). The preferred mixing unit is according to unit B below.

As discussed above a plurality of microchannel structures may be arranged around a spinning axis combined with using centrifugal force created by spinning around the spinning axis for driving the liquid flow in parallel through the structures. Centrifugal force may be combined with capillary force. Other forces may also be used for this and other configuration. See for instance under the heading "Means for driving the liquid flow".

In particular a plurality of the microchannel structures may be present on a microfluidic device that has an axis of symmetry coinciding with a spinning axis. In this variant the microchannel structures are typically arranged to permit the use of centrifugal force for driving a liquid flow in parallel within individual microchannel structures. See above under the heading "Microfluidic device".

The retaining microcavity (219) may have different forms as known in the field. Preferred variants often define or are part of a U/Y-shaped structures, possibly linked to upwardly bent microconduits at either one or both of the upwardly directed shanks of the U/Y as described previously for reaction microcavities (WO 0040750, WO 0146465). The U-shaped structure may also be as presented in FIG. 2e where the U is defined by a reaction microcavity which comprises two upwardly directed shanks, the upper parts of which are connected to microconduits (218,220) containing the anti-wicking means/valves (221e,a). Microconduit (218) plus the most downstream part of the retaining microcavity (219) define an upward bent that will provide a valve function. This latter variant may be advantageous in the case the mixed aliquot is to be transported further downstream in the structure. See FIGS. 2a–b and e. Another variant is that the microcavity (219) is circle like with the down stream or upstream microconduit attached without formation of this kind of bent. See for instance FIG. 2e in which one of the microconduits (242) is a pure air channel which preferably has an hydrophobic inner surface that in fact creates an anti-wicking effects and renders passage of liquids difficult.

The mixed aliquot may be retained in the microcavity (219) for different purposes, such as performing a chemical and/or biochemical reaction and/or a measurement of one or more chemical or physical parameters of the mixed aliquot under static non-flow conditions within the microcavity (219) with a high accuracy (that would have suffered from loss of liquid and changes in concentrations if wicking and evaporating would have been allowed to act). Typically the reaction and/or measurement are part of an assay procedure for determining/detecting a component present in the mixed aliquot or in some other aliquots dispensed to the microchannel structure. The reaction may also be performed for synthetic purposes. Biochemical reactions include bioaffinity reactions (e.g., reactions between an antibody and an antigen/hapten, an enzyme and its substrate, cofactor, cosubstrate etc., complementary nucleic acids, and lectin carbohydrate) including enzyme reactions, cell reactions, etc. The reactions may take place in a homogeneous liquid phase or involve reactions between solid phase bound reactants and dissolved reactants or reactants in suspended form (heterogeneous reactions). Retaining may also be for the storing of the mixed aliquot, for instance awaiting certain process steps to take place outside or inside the microfluidic device on other aliquots that are to be used in the microfluidic device, possibly together with the mixed aliquot. The periods of time for retaining are as outlined in the first object. After the retaining period has lapsed, further processing of the liquid aliquot may take place in the reaction microcavity (219) or further downstream in the microchannel structure.

The surface tension of the liquid, the liquid contact angles of the inner surfaces of the microchannel structures, kind of liquids etc. are selected as described under the headings "Microfluidic device", "Valve functions" and "Anti-wicking means".

The use of unit A is defined by the method of the second main aspect of the invention and comprises in addition a mixing step utilizing the mixing subunit and a process step of the mixed aliquot that may be performed for any of the reasons discussed above.

B. Unit B: Mixing Unit

The second subaspect of the invention is a microfluidic device as defined herein comprising a microchannel structure in which there is a structural unit accomplishing mixing of aliquots (unit B).

This subaspect is based on our recognition that quick, efficient and reliable mixing of aliquots that are miscible can take place by first collecting the aliquots in a microcavity, preferably under the formation of a phase system, and then permitting the aliquots to pass through a microchannel of sufficient length to permit homogeneous mixing.

Figure 2C:
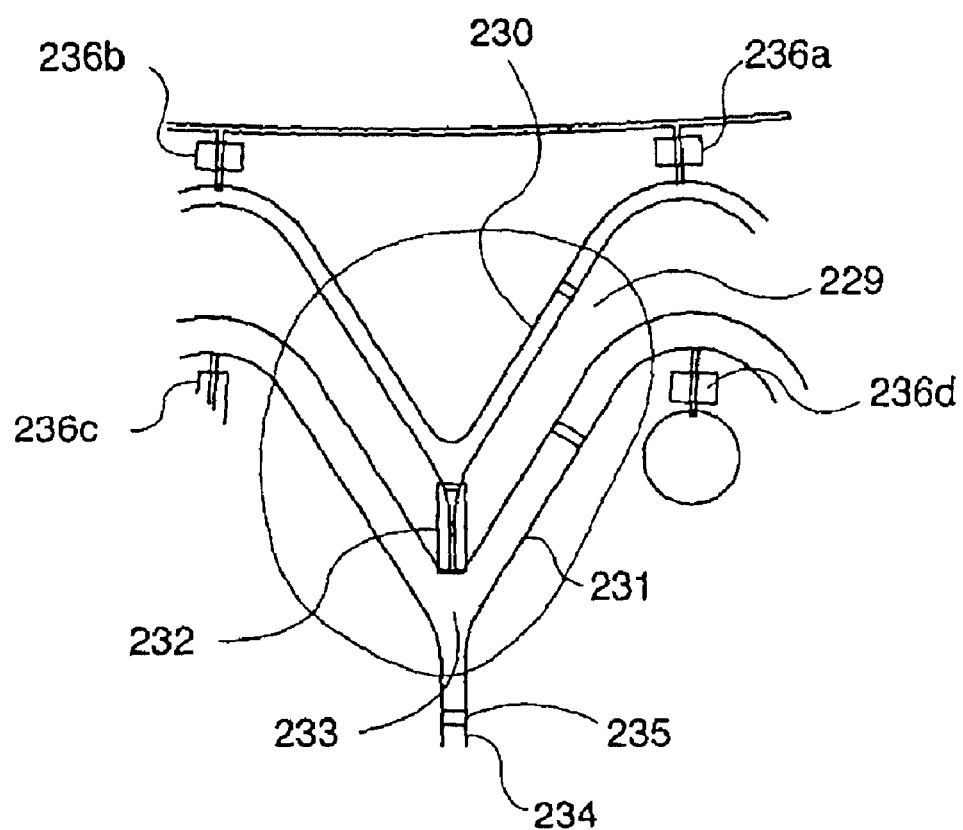
Figure 2D:
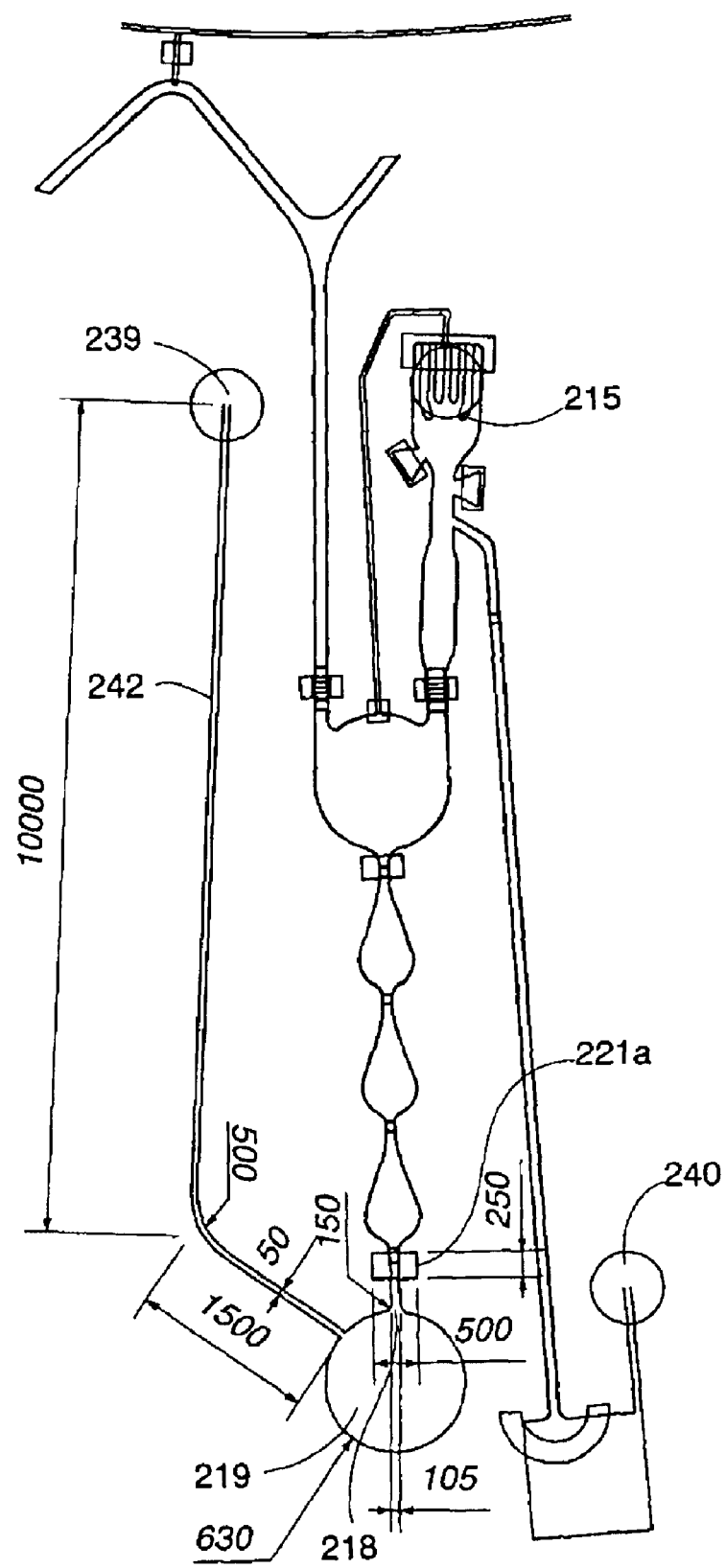
Figure 2E:
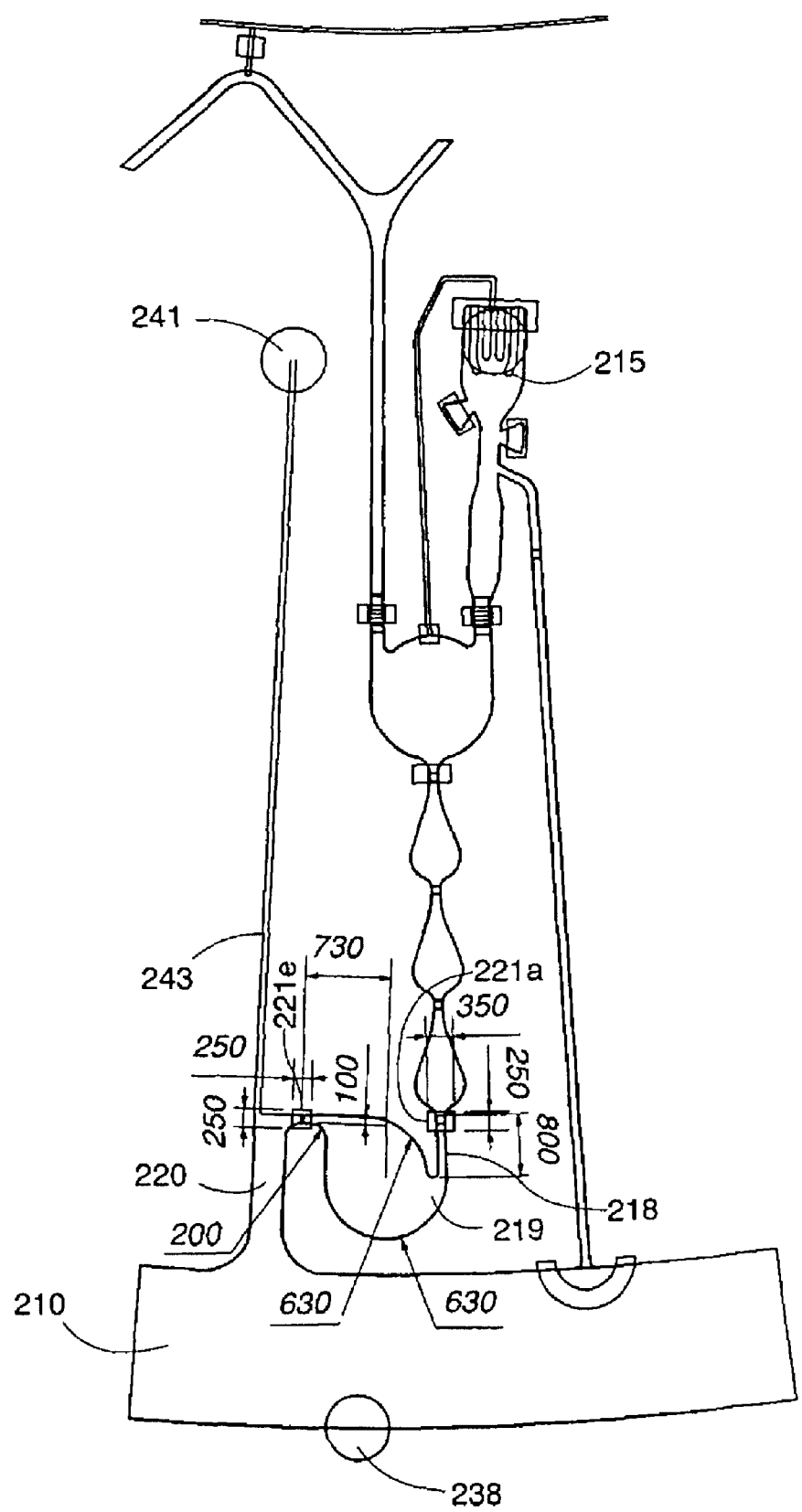

Preferred variants of our mixing units are illustrated in FIGS. 2a–c. The variants shown are arranged as discussed above on a spinnable substrate (compare the arc-like arrangement). FIGS. 2a–b comprises four microchannel structures connected to each other by a common distribution channel.

In general terms unit B comprises an inlet arrangement (201) and a mixing microconduit (202) as described in prior publications. Between the inlet arrangement (201) and the mixing microconduit (202) we have introduced a microcavity (203) to precollect the aliquots to be mixed in the mixing microconduit (202). The precollecting microcavity (203) has an opening (223) in its lower part which opening is in register with the mixing microconduit (202). This precollecting microcavity may have various designs with one feature being that it should enable formation of a liquid interface between the two aliquots to be mixed. The flow direction should be essentially perpendicular at the interface, i.e., 90°±45°.

In addition to the mixing unit as such, FIGS. 2a–b show:

(a) A common distribution channel (204) as described for unit C below with an inlet port (205) with ridges/projections (206,216) as described for unit D above, an outlet port (207), and inlet vents (208) to ambient atmosphere via a common venting channel (209) and an air inlet (237). When the distribution channel is filled with liquid and a downward driving force is applied, liquid will be forced out through the microconduits connecting the distribution channel (204) with the microcavities (203). At the same time air will enter through the vents (208);

(b) A common waste channel (210) comprising outlet ports (238);

(c) Volume-defining units (213) as described for unit E and comprising anti-wicking means (214,221g) as described above, an inlet port (215) with ridges/projections (206,216) as described for unit D, and an overflow channel (217) ending in an outlet (212) in the common waste channel (210); and (d) A microcavity (219) in which various kinds of processes may be carried out as discussed elsewhere in this specification, and an enlarged waste outlet conduit (220), which merges into the common waste channel (210) via the outlet (211).

Surface breaks (non-wettable) are represented by straight or arc-formed rectangles (e.g., 221a,b,c etc. and 222, respectively).

The mixing unit of the present invention is characterized by comprising (a) the microcavity (203) with an outlet opening (223), typically in its lower part; (b) an inlet arrangement (201) linked to the microcavity (203), and (c) a mixing microconduit (202) connected to the outlet opening (223). The microcavity (203) shall have a volume sufficient to contain simultaneously the aliquots to be mixed. The inlet arrangement is connected to the upper or lower part of the microcavity (203).

Preferably there is a valve associated with the mixing conduit (202), preferably close to its joint to microcavity (203). This valve function is preferably an inner valve of the same kind as discussed elsewhere in this specification, for instance in the form of a surface break (non-wettable) (221b). The valve may also be mechanical.

The inlet arrangement may comprise a common inlet microconduit (not shown) for several aliquots and/or separate inlet microconduits (224 and 225) for individual aliquots. The joint between these microconduits and the inlet openings are preferably located at the upper part of precollecting microcavity (203). In the upstream direction each of these inlet microconduits (224 and 225) communicates with an inlet port (205 and 215). Each inlet microconduit (224 and 225) may comprise a submicrocavity permitting separate predispensing of an aliquot to a microchannel structure before transport down into the microcavity (203). In FIGS. 2a–b one of these submicrocavities is microcavity (226) of the volume-defining unit (213) and the other Y-shaped structure (227) a part of which belongs to the common distribution channel (204). Between each submicrocavity (226,227) and microcavity (203) there may be a valve function (221d,c, respectively) that enables for aliquots to be transported into the submicrocavities (226,227) without leakage into the microcavity (203). The valve function at these positions is preferably an inner valve of the same kind as discussed for the valve functions (221a,b) associated with the mixing microconduit (202), e.g., a surface break (non-wettable) (221a,b).

As illustrated in FIGS. 2a–b the mixing conduit (202) may have various forms. It may be a single channel that is meandering or coiled in order to save space as suggested in FIG. 2a. It may also be built up of a chain of interlinked small microcavities (228), each of which has a smoothly increasing cross-sectional area from the inlet end and a smoothly decreasing cross-sectional area when approaching the outlet end as suggested in FIG. 2b. FIG. 2b also illustrates that these small microcavities can be of continuously increased breadth from their inlet and outlet ends with the steepest increase from the outlet end (droplet-shaped breadth).

When the aliquots are introduced into microcavity (203) there should be formed a phase system in the microcavity. Each aliquot should be represented by a liquid phase. The flow direction out of the microcavity (203) should be essentially perpendicular to the interface between the phases. During passage of the phase system into the mixing microconduit (202), the upper phase is typically entering in the center of the microconduit and the lower phase next to the inner wall. Mixing will occur during the transport in the microconduit (202) probably due to the fact that the center of the liquid flow will have a higher flow rate than the peripheral part next to the inner wall of the mixing conduit. This means that the two aliquots repeatedly will replace each other in the front position while traveling through the mixing microconduit. This may be the reason for the quick and efficient mixing that is accomplished in the inventive mixing structure. If the mixing microconduit (202) is of sufficient length in relation to the flow rate and the constituents of the aliquots, complete mixing will have occurred at the end of the mixing microconduit (202). Sufficient length typically means that the phase system should have a smaller volume than the volume of the mixing microconduit (202).

FIG. 2c shows a third variant of the inventive mixing unit. This variant has a microcavity (229) corresponding to microcavity (203) in FIGS. 2a–b. The microcavity (229) comprises an upper downward bent (230) and a lower downward bent (231) and a channel part (232) going from the lower part of the upper bent (230) to the lower part of the lower bent (231). In the lower part of the lower bent (231) there is an opening (233) leading into a mixing microconduit (234). Preferably there is a valve (235) in the mixing microconduit (234), typically close to the opening (233). This valve preferably is an inner valve for instance comprising a change in surface characteristics (non-wettable surface break). FIG. 2c in addition shows inlet vents to ambient atmosphere (236a–d) at top positions of the bents. When filling the downward bents with aliquot 1 and aliquot 2, respectively, a liquid interface can be formed in the communicating microconduit (232). By applying a downwardly directed driving force the two aliquots will be forced into the mixing microconduit in the same manner as for the variants described in FIGS. 2a–b.

In the variant of FIG. 2c, the inlet arrangement of FIGS. 2a–b is fully integrated with the precollecting microcavity (203) and therefore more or less indistinguishable.

The microcavity (229) of FIG. 2c may be part of two aligned common distribution channels of the same kind as outlined in FIGS. 2a–b.

In preferred variants, a microchannel structure comprising unit B may be oriented about a spinning axis that in turn may coincide with an axis of symmetry of a spinnable substrate/device as discussed elsewhere in this specification. The flow direction through the outlet opening of microcavity (203) is typically oriented essentially outward in relation to the axis of symmetry (spinning axis).

The use of unit B comprises a method for mixing two or more aliquots within a microfluidic device comprising a microchannel structure. The aliquots may have the same or different volumes and/or compositions. The method is characterized in comprising the steps of: (i) providing a microchannel structure comprising unit B as defined above; (ii) introducing the aliquots via the inlet arrangement of unit B into microcavity (203), preferably to form a phase system therein; (iii) applying a driving force to transport the phase system through mixing microconduit (202); (iv) collecting the homogeneously mixed aliquots at the end of the mixing microconduit (202) for further transport and/or treatment within the microchannel structure.

If submicrocavities (226,222) are present in the inlet arrangement (201), the aliquots to be mixed may be individually predispensed to these submicrocavities before the driving force for transport into precollecting microcavity (203) is applied.

The rules for selecting driving force are the same as discussed as discussed above. For spinnable substrate centrifugal force is preferred.

At least one of the aliquots should have a surface tension, which is $\geq 5$ mN/m, such as $\geq 10$ mN/m or $\geq 20$ mN/m.

Common waste channel: In FIGS. 2a–b the common waste channel (210) have supporting means for minimizing the risk for collapse due to the breadth of the channel. The surface break (227) improves the emptying of the overflow channel (217) and facilitate its refilling.

C. Unit C: Unit for Forming a Plurality of Aliquots of Defined Volumes within a Microfluidic Device, Distribution Manifold The third subaspect of the invention is a microfluidic device comprising a microchannel structure in which there is a structural unit (unit C) accomplishing metering one, two, three or more aliquots (two or more=plurality of aliquots).

This subaspect is based on our recognition that the relative loss of liquid by evaporation may be significant when dispensing small aliquots, in particular nl-volumes, to individual microchannel structures in a microfluidic device. We have also found that the prior systems utilizing a common reagent fill channel from which metering is done in parallel in a plurality of metering microcavities are insufficient when the cross-sectional dimensions of the channels are in the lower part of the μm-range and/or the volumes are decreased into the nl-range.

Figure 3A:
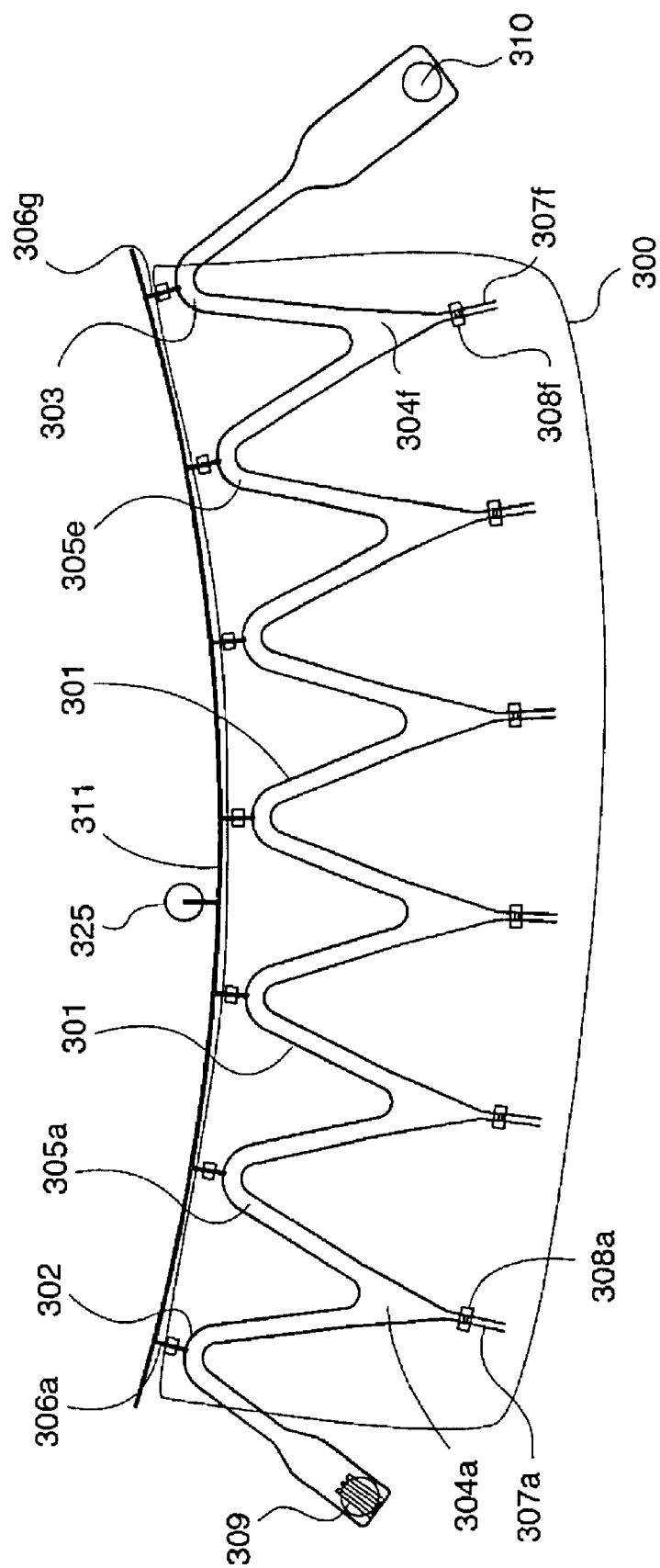

Unit C presents a solution to these problems and makes it possible to reproducibly meter a number of smaller aliquots within the same microfluidic device and to transport these aliquots in parallel into separate microchannel structures of the microfluidic device or into separate parts of the same microchannel structure. The aliquots may be identical or different with respect to size, composition etc., and are typically in the nl-range as defined above Unit C is represented in FIGS. 3a–c that show variants that are arranged about a spinning axis that may coincide with an axis of symmetry as discussed above. In these figures the distribution unit as such is encircled (300).

Based on FIGS. 3a–b, the unit comprises: (a) a continuous microconduit (301) containing an upper part at each end (end parts, 302, 303) and therebetween alternating lower and upper parts (304a–h/f and 305a–e, respectively); (b) the number of upper parts including the end parts is n and the number of lower parts is n-1 where n is an integer >2, i.e., $\geq 3$; (c) each of the upper parts (302, 303, 305a–e/g) has means for venting (top vent, inlet vents) (306a–g/i) to ambient atmosphere and/or anti-wicking means (326a–i) in length-going edges delineating its lower wall(s); (d) each of the lower parts (304a–f/h) has an emptying opening which in a downstream direction via a connecting microconduit (307a–f/h) communicates with a substructure of a microchannel structure and/or with a corresponding substructure of another microchannel structure; (e) each of the connecting microconduits (307a–f/h) has a valve (308a–f/h), i.e., a valve function in close association with the joint between the connecting microconduit and the corresponding lower part; (f) an inlet port (309) is connected to the continuous microconduit (301) directly or indirectly at one of the upper parts (302, 303, 305a–e/g), preferably via one of the end parts (302 or 303); and (g) an outlet port (310) is connected to the continuous microconduit (301) directly or indirectly at another upper part (302, 303, 305a–e/g), preferably via one of the end parts (302 or 303) (which preferably is not connected to the inlet port, i.e., an inlet port and an outlet port should not connected at the same upper part).

In a lower part (304a–f/h), the continuous microconduit (301) is preferably shaped as a downward bent. This kind of bents includes that the microconduit in the bent is enlarged t) a microcavity. Similarly an upper part is preferably in the form of an upwardly bent microconduit but without enlargement of the type that can be present in a downward bent.

The smallest cross-sectional areas of the continuous microconduit (301) between the ends (302, 303) should be in the upper parts, with preference for in association with the top vents (306a–g/i) and/or the anti-wicking means (326a–i). The cross-sectional area of the continuous microconduit (301) may be of constant size and/or shape along the length of the continuous microconduit.

The inlet ports (309) and the outlet ports (310) are typically at a lower level than the extremes of the upward bents and may even be at a lower level than the extremes of the lower parts (304) and/or than a desired part of the individual microchannel structures that are downstream the lower parts (304) (for instance at a lower level than a waste outlet port).

The liquid aliquot is preferably transported from an inlet port (309) to an outlet port (310) of the continuous microconduit (301) by capillarity meaning that the liquid contact angle in this part of the microchannel structure continuously has to be well below 90°, i.e., preferably ≦40°, such as ≦30° or ≦20°, and enabling filling by capillarity of the continuous microconduit (301) to valves (308a–f/h) by self-suction from an inlet port of the microconduit (301).

In the preferred variants the continuous microconduit (301) has meander-form.

The integer n is preferably >2, such as 3, 4, 5, 7, 8, 9, 10, 11, 12 or more.

The joints between a connecting microconduit (307a–f/h) and a lower part (304a–f/h) are preferably located at the same level and/or at the lowest part of a downward bent. The valves (308a–f/h) in the connecting microconduit (307a–f/h) preferably are inner valves that may be closing or non-closing.

The top vents (306a–g/i) are preferably located at the same level on the upward bents (302, 303, 305a–e/g). Each top vent (306a–g/i) comprises an opening in an upper part (302, 303, 305a–e/g) of the continuous microconduit (301) and possibly also a microconduit. Each top vent may have an inner valve and/or may be equipped with anti-wicking means in the case the top vent has a length-going edge that might promote imbibing and evaporation of liquid. The anti-wicking means are described elsewhere in this specification. The top vents may be connected via a common venting channel (311) and an inlet (325) to ambient atmosphere.

The openings associated with top vents in the upper part may be directed upward as illustrated in FIGS. 3a–c but may also be directed in other directions, e.g., as illustrated in FIG. 2c (236a–d).

As outlined for unit D preferred variants of unit C may have: A) inlet port (309) designed with a hydrophobic surface break at the rim of the inlet opening which directs a dispensed aliquot into the opening of the port, and B) an inner valve in the microconduit connecting an upper part to an inlet port (310). Compare also FIG. 7 and FIG. 8 of WO 2002075775 and WO 2002075776, respectively, which are incorporated herein by reference.

One or both of the end parts (302,303) may directly or indirectly be connected to another distributing unit C according to the invention as illustrated in FIG. 2 of WO 2002075312, which is incorporated herein by reference.

Unit C is intended for distributing (n-1) aliquots to (n-1) microchannel structures or (n-1) part structures of a microchannel structure. The volume between two close top vents (306a–e/g) will in most variants define the volume of the aliquot to be dispensed through the connecting microconduit (307a–f/h) between these top vents (segment). By varying the depth and/or width of different segments, one can envisage that the volumes dispensed through different connecting microconduits (307a–f/h) can differ in a controlled manner.

By first filling the continuous microconduit (301) with liquid between its end parts (302 and 303), for instance by self-suction, and then forcing liquid to pass through the connecting microconduits (307), the metered aliquots between close top vents will pass into separate connecting microconduits. Spillover between neighboring segments of the continuous microchannel (301) will be minimized due to the top vents and/or by the presence of anti-wicking means (326) in edges delineating lower walls in upper parts.

By filling the segments with the same liquid, for instance in one step, aliquots of the same composition will be dispensed through all the emptying openings.

FIG. 3b illustrates a non-meander form of unit C (straight form) in which the lower parts (304a–h) are in form of microcavities that are connected to each other via upper parts (305a–g). At the end of the continuous microconduit (301) there are also upper parts (302,303) via which an inlet and an outlet port may be connected (309 and 310, respectively). Means for venting (306a–i) the continuous microconduit (301) may be associated with upper parts of the continuous microconduit, for instance in the conduit parts (305a–g) and/or in the end parts (302,303). The lower part of each microcavity (304a–h) has an outlet opening to which a connecting microconduit (307a–h) with a valve function (308a–h) is associated. There may also be anti-wicking means (rectangles, 326a–i) at both sides of each microcavity (304a–h) in edges that extend down into a neighboring microcavity/lower part (304a–h). The anti-wicking means may be of the same kind as discussed elsewhere in this specification. A variant is shown in FIG. 7 and FIG. 8 of WO 2002075775 and WO 2002075776, respectively, which are incorporated herein by reference, and illustrates a distribution manifold with a centrally located inlet port and anti-wicking means in the edges as discussed above but without the top vents (306a–g).

FIG. 3c represents a variant, which will enable distribution of aliquots of different compositions to individual microchannel substructures. The distribution unit as such is encircled (300). Upstream the distribution unit (300) there is a microchannel substructure (311), which will enable filling of segments between close top vents (306a–d) of the continuous microchannel (301) with aliquots of different compositions. In order to accomplish this, substructure (311) comprises a volume-defining unit (312), which is capable of metering a liquid volume that is equal to the volume of the segment between two close top vents (306a–d) in the continuous microchannel (301). If the volumes of the segments are different, subunits defining different volumes may be included in substructure (311). In FIG. 3c, the substructure (311) upstream the distribution unit (300) may comprise further functionalities. Thus substructure (311) may comprise a first downward bent (313) which has one of its shanks (314) connected to the end part (302) of the continuous microchannel (301) and the other shank (315) connected to the lower part of a second downward bent (316) that in turn is connected to a metering part of volume-defining unit (312) at the upper part of one of its shanks (317). The other shank (318) of the second downward bent (316) may be venting to ambient atmosphere via an inlet (327). The illustrated metering part of volume-defining unit (312) is of the same kind as unit E and includes an overflow system and an inlet port (319) of the same kind as unit D. The volume of the metering microcavity (320) of the volume-defining unit (312) is the same as in a segment between two close top vents (306a–d). The substructure (311) of FIG. 3c also comprises (a) a large waste chamber (321) with a relatively wide opening (322) into the lowest part of the first downward bent (313), and (b) a valve function (323) associated with the connection between the first and second downward bent (313,316).

Due to the size of the waste chamber (321) there are supporting means in form of pillars (324) securing that its top and bottom are kept apart from each other.

The kind of design presented in FIG. 3c makes it possible to consecutively fill the segments between the top vents (306a–d) of the continuous microconduit (301) with aliquots of different compositions, and thus to distribute aliquots of different composition to the individual substructures connected to unit C via the connecting microconduits (308a–c). With reference to FIG. 3c this means (presuming waste chamber (321) is closed or absent):

Step 1: Aliquot 1 is metered in the volume-defining unit (312) and transported to downward bent (313), for instance by spinning if the unit is present on a spinnable substrate that may be a circular disc by the hydrostatic pressure created by centrifugal force.

Step 2: Aliquot 2 is metered in the volume-defining unit (312) and transported into the downward bent (313). This will push aliquot 1 to segment 1 (between top vents 406a and b) of the continuous microconduit (301).

Step 3: Aliquot 3 is metered in the volume-defining unit (312) and transported into the downward bent (313). This will push aliquot 1 to the second (next) segment and place aliquot 2 in the first segment.

When the desired number of segments has been filled a downwardly directed driving force is applied to pass the aliquots through their respective connecting microconduit/valve (307a–c/308a–c).

A simplified variant of FIG. 3c means that the first downward bent (313) is designed as a volume-defining unit, for instance by placing an overflow system at the same level as the top vents (306a–d) of the continuous microconduit (301) in shank (315).

By introducing a chemical functionality, for instance in the form of substructure comprising an inlet port followed by a reaction zone in front of unit C, unit C may be used for collecting separate fractions between each pair of neighboring top vents in the continuous microconduit (301) from liquids that have passed through the reaction zone. Collected fractions can then be further processed, for instance analyzed, by taking them further down into the microchannel structure via the connecting microconduits (307a–c). With respect to FIG. 3c, such a zone suitably is positioned between the first and second downward bents (316 and 313, respectively), for instance combined with the valve (323).

The reaction zone may for instance comprise an immobilized reactant selected from (a) a catalysts such as an enzyme, (b) a ligand capable of binding to a component of a liquid which is to pass through the zone, (c) an affinity complex between a ligand and a binder etc. Based on the presence of particular components in the fractions that are collected one can analyze for features related to the zone as such or to the liquids applied, e.g., features of compounds present in the zone and/or in a fraction.

Unit C is preferably present in a spinnable microfluidic device of the kind discussed elsewhere in this specification. The continuous microconduit (301) may then be oriented in an annular-like fashion around a spinning axis and may occupy at least a sector of an annular zone defined by the continuous microconduit. The sector typically covers at least 0.5–10° and at most 360° relative a spinning axis and/or an axis of symmetry. The lower parts (304) of the unit are directed outwards from the spinning axis and the upper parts (302, 303, 305) inwards towards the spinning axis.

The driving force is selected according to the same principles as outlined for the microfluidic device above, with preference capillarity for filling the continuous microconduit (301) and centrifugal force or overcoming the valve functions (308a–f/h) in the connecting microconduits (307a–f/h).

The aliquot applied should have a surface tension, which is $\geq 5$ mN/m, such as $\geq 10$ mN/m or $\geq 20$ mN/m.

D. Unit D: Inlet Unit with Means supporting Liquid Entrance into a Microchannel Structure This subaspect of the invention refers to an improvement that lowers the time for undesired evaporation of an aliquot that has been dispensed to a microfluidic device of the same kind as the invention. The advantages are primarily related to dispensing and/or metering nl-aliquots within microfluidic devices.

The fourth sub-aspect of the invention is a microfluidic device comprising a microchannel structure in which there is an inlet unit promoting liquid entrance into a microchannel structure.

Figure 4A:
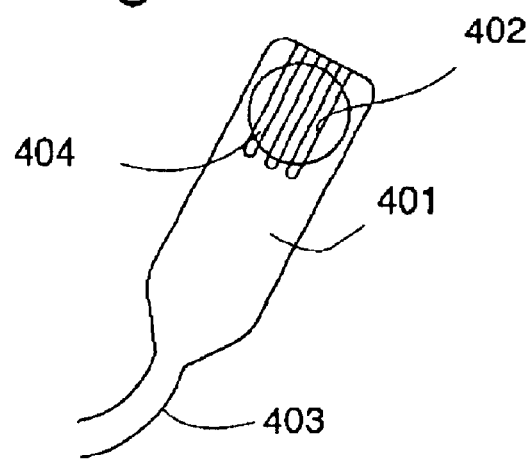
FIG. 4A–FIG. 4B illustrate innovative variants of unit D.
Figure 4B:
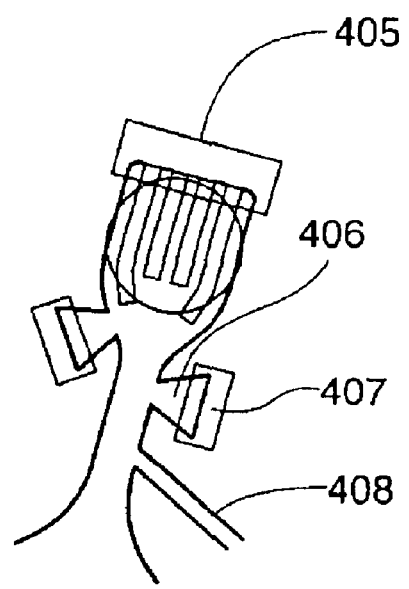

The unit is illustrated in FIGS. 4a–b. The unit comprises: (a) an inlet port comprising a microcavity (401) and an inlet opening (402), and (b) an inlet conduit (403) which is positioned downstream said microcavity (401) and which communicates with the interior of the microchannel structure.

The inner wall of the microcavity (401) comprises one or more grooves and/or projections (ridges/valleys) (404) directed towards the connection between the inlet conduit (403) and the microcavity (401). The microcavity (401) is typically tapered (narrowing) when approaching the inlet microconduit (403).

The main purpose of the grooves and/or the projections is to increase the capillary suction in the inlet port. This will speed up liquid penetration and lower the time for undesired evaporation and loss of liquid during the dispensing operation.

The narrowing design of microcavity (401) as such assist in promoting liquid penetration and of retaining a dispensed aliquot within the covered part of a microchannel structure.

FIG. 4b illustrates a variant comprising a non-wetting surface break (405) in association with the rim of the inlet opening (401), primarily at a side which is closest to the spinning axis if the inlet port is located on a spinning substrate. This figure also illustrates a variant of unit D that comprises anti-wicking means downstream the inlet opening (401). These means may comprise changes in geometric surface characteristics (406) and/or in chemical surface characteristics (407).

The projections may have a height that at maximum is equal to the depth of the microcavity (401) but may be significantly lower as long as a sufficient capillary action (self-suction) is maintained in the inlet port in order to draw a dispensed aliquot completely into the covered part of a microchannel structure.

The liquid to be introduced typically has a surface tension as discussed above.

The width of the inlet opening is typically smaller than the width of microcavity (401) as illustrated in FIGS. 4a–b.

The inlet opening (402) may have one or more edges directed inwards the port, preferably with an n-numbered axis of symmetry perpendicular to the opening. n is preferably an integer $\leq 7$, such as 3, 4, 5 or 6. See for instance U.S. Pat. No. 4,233,029 (Eastman Kodak) and U.S. Pat. No. 4,254,083 (Eastman Kodak).

Unit D is typically combined with a dispenser that is capable of dispensing an aliquot in the nl-range to the inlet port. The dispenser can be one of the dispensers generally described elsewhere in this specification.

Other forces than capillary force may be used for promoting penetration through the inlet port, for instance inertia force including centrifugal force.

Microchannel structures that comprise unit D are in a preferred variant placed on a spinnable substrate as discussed elsewhere in this specification.

This kind of inlet unit is particularly well adapted to receive aliquots that are in the form of particle suspensions.

E. Unit E: Definition of the Volume of Aliquots

In spite of the previously known devices for metering aliquots in the µl-range there is still a need for improvements, in particular with respect to the nl-range. The reason is that uncontrolled evaporation has a stronger influence on a smaller aliquot more compared to a larger aliquot (respect relative loss in volume). This is further accentuated when a large number of aliquots are to be dispensed in sequence before the aliquots are further processed within a microfluidic device.

The present inventors have recognized these problems and designed a volume-metering unit (unit E) to meter primarily nl-volumes of liquids. The unit can be integrated into microchannel structures of microfluidic devices.

The fifth subaspect of the invention thus is a microfluidic device that comprises a microchannel structure in which there is volume-defining unit enabling accurate metering of small volumes within a microfluidic device, primarily nl-volumes.

Figure 5:
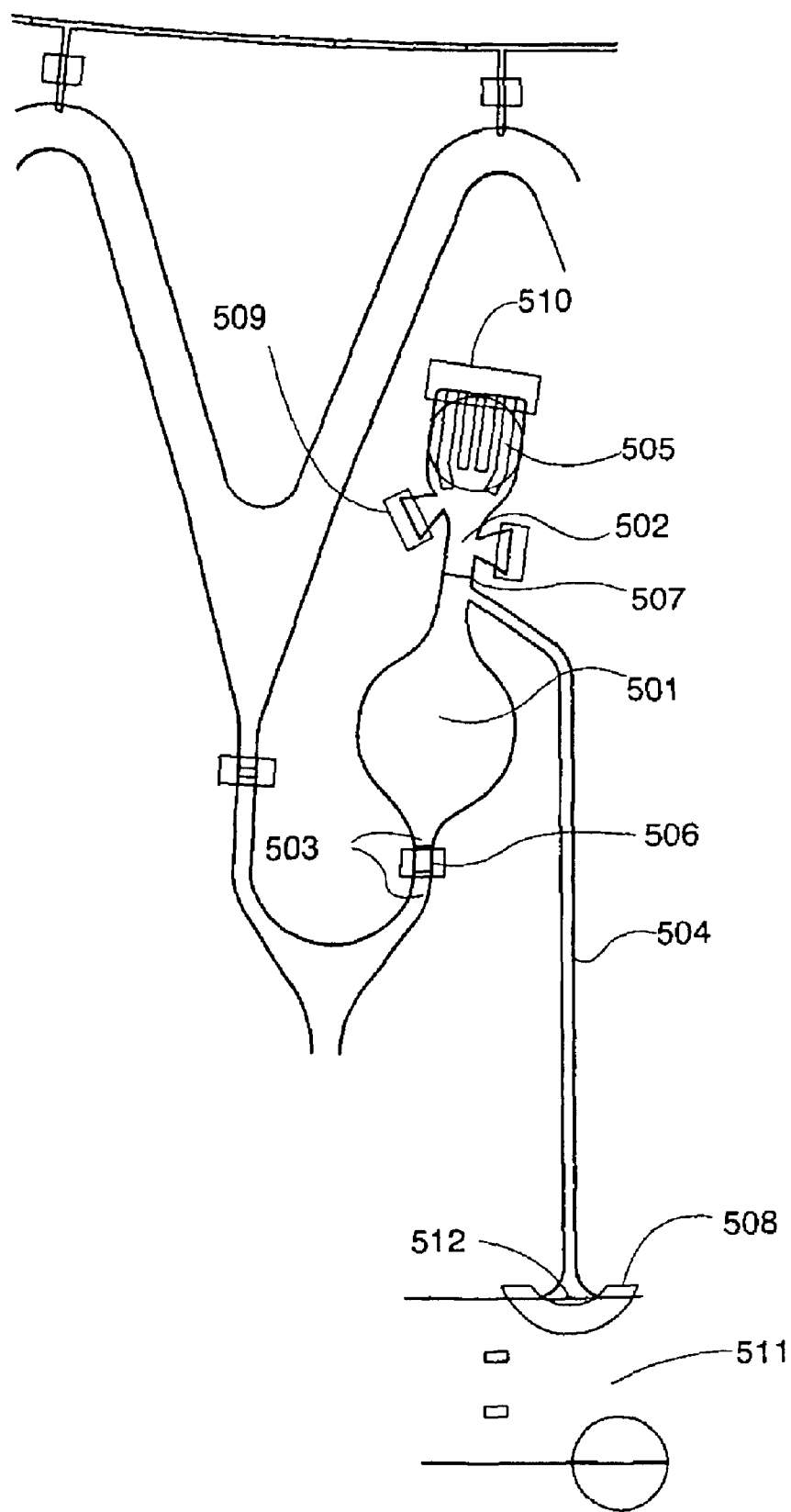
FIG. 5 illustrates an innovative variant of unit E.

Unit E is illustrated in FIG. 5. Unit E comprises: (a) a volume-defining microcavity (501); (b) an inlet microconduit (502) which is connected to the microcavity (501) via an inlet opening on the microcavity (501) (at the joint between said microcavity and the inlet microconduit), (c) an outlet microconduit (503) which is connected to microcavity (501) via an outlet opening in microcavity (501) (at the joint between said microcavity and the outlet microconduit), and (d) an overflow microconduit (504), which is connected to an overflow opening on microcavity (501) (at the joint between said microcavity and the overflow microconduit).

The inlet opening and the overflow opening are typically at the same level on the microcavity (501). The overflow opening is at a higher level than the outlet opening and the volume between these two openings defines the volume to be metered in the volume-defining microcavity (501). The metered volume is typically in the nl-range as defined above, but may also be larger, such as ≦10 µl or ≦100 µl or ≦1000 µl.

The liquid typically has a surface tension as discussed above.

The overflow microconduit (504) is typically communicating with ambient atmosphere via an enlargement at the end of the overflow microconduit (504) (typically a waste chamber or a waste conduit (511). The joint between the overflow microconduit (504) and the enlargement is at a lower level than both the connection between the overflow microconduit (504) and the lowest part of the volume-defining microcavity (501) (in reality the valve function (506) at the outlet opening of the volume-defining microcavity).

The outlet microconduit (503) is used to transport a metered liquid aliquot further into the microchannel structure.

The volume-defining microcavity (501) may have different forms, for instance comprise: (a) one or more capillaries, and (b) a downward bent structure with one shank acting as the inlet and the other shank ending in an upward bent that can be used as the overflow microconduit, and with the outlet microconduit (503) being joined at the lower part of the downward bent and intended for transporting a metered aliquot further downstream in the microchannel structure.

The cross-sectional area $(a_1)$ in the volume-defining microcavity (501) at the overflow opening is in preferred variants smaller than the largest cross-sectional area $(a_2)$ between the overflow opening and the outlet opening (506). The ratio $a_1/a_2$ typically is $\leq \frac{1}{3}$, such as $\leq \frac{1}{10}$. This means a significant constriction of the microcavity (501) at the joint between the overflow microconduit (504) and the microcavity (501), i.e., at the joint between inlet microconduit (502) and volume-defining microcavity (501).

The inlet microconduit (502) upstream the overflow opening typically widens, for instance to an inlet port (505), such as unit D.

Between the volume-defining unit and a true inlet port there may other structural/functional units, for instance a unit for sample treatment such as for the removal of particulate materials.

Unit E may have a valve function (506,507,508) associated with at least one of (a) the outlet opening of microcavity (501), (b) the inlet microconduit (502) closely upstream the overflow opening, and (c) the overflow microconduit (504), preferably its lower part such as in association with its joint with the waste conduit/chamber (511).

These valves may be mechanical valve or of any of the other types discussed above, but is preferably an inner valve of the closing or non-closing type with emphasis of the former.

At least one of the inlet microconduit (502), the outlet microconduit (503) and the overflow microconduit (504) may have anti-wicking means of the kinds defined elsewhere in this specification. The variant shown in FIG. 5 comprises anti-wicking means (509) in the inner edges of inlet microconduit (502). The anti-wicking means stretches across the corresponding inner walls as discussed above in general terms.

A microchannel structure comprising unit E may in its preferred variants be equipped with valve functions (506, 508), preferable inner valves of the non-closing type, and be present on a spinnable substrate as discussed elsewhere in this specification. If the intention is to drive the liquid out of the overflow channel (504) before the metered aliquot is released via the outlet microconduit (503), it becomes important to have a sufficiently large difference in radial distance $(r_1)$ between the overflow opening in the volume-defining microcavity (501) and the ending (512) of the overflow microconduit (504) in a waste chamber (511) relative to the difference $(r_2)$ in radial distance between the overflow opening and the valve (506) in the outlet microconduit (503). $r_1$ shall be essentially larger than $r_2$. This particularly applies if the valve function (506) in the outlet microconduit (503) is an inner non-closing valve. By properly selecting $r_1 > r_2$, e.g., $r_1 > 1.25 r_2$, or $r_1 > 1.5 r_2$, or $r_1 > 2 r_2$, or $r_1 > 5 r_2$, or $r_1 > 10 r_2$, it will be possible for the liquid in the over-flow microconduit to pass through the valve (508) at a lower driving force (e.g., lower spinning speed) than required for the liquid in the volume-defining microcavity to pass through the valve (506). The optimal relation between the two distances depends on various factors, such as width, breadth, wettability, roughness etc. of the microconduits concerned as well as surface tension, density et of the liquid concerned.

A variant that may be adapted to spinnable substrates comprises a downward bent with the volume-defining microcavity being a part of the lower part of the bent. The overflow microconduit typically is connected to one of the shanks of the downward bent and forms together with this shank an upward bent. The upper part of the same shank vents to ambient atmosphere (inlet vent). An inlet port for sample (corresponds to 505) may be connected to the other shank of the same downward bent. The vent to ambient atmosphere may be designed with a sample/liquid inlet function. The outlet conduit with a valve is connected to the lower part of the downward bent (corresponds to 503 and 506, respectively). The overflow microconduit (corresponds to 504) ends in a waste channel or waste chamber with a valve function (corresponds to 508).

There are advantages with having the outlet opening connected to the outlet microconduit (503) on microcavity (501) somewhat higher than the lowest part of the volume-defining microcavity. In such variants there will be a small volume present below the outlet opening in which it will be possibly to sediment and collect particulate materials and only flow the supernatant that corresponds to a metered volume through the outlet microconduit (503). Sedimenting can be assisted by the use of centrifugal force (spinning).

The use of unit E defines a method for introducing metered aliquots into microchannel structures. The method comprises the steps of: (i) providing a microchannel structure comprising unit E and an aliquot having a larger volume than then the volume to be metered in the unit; (ii) introducing the liquid of aliquot into the unit; (iii) applying a first driving force to move excess liquid out through the overflow microconduit (504) and a second driving force to move the metered volume through the outlet microconduit (503) into the remaining part of the microchannel structure.

The driving force is selected as discussed above for the other units with preference for inertia force including centrifugal force when the substrate is spinnable.

Although the present invention and its advantages have been described in detail, it should be understood that various changes, substitutions and alterations can be made herein without departing from the spirit and scope of the invention as defined by the appended claims. Moreover, the scope of the present application is not intended to be limited to the particular embodiments of the process, machine, manufacture, composition of matter, means, methods and steps described in the specification. As one of ordinary skill in the art will readily appreciate from the disclosure of the present invention, processes, machines, manufacture, compositions of matter, means, methods, or steps, presently existing or later to be developed that perform substantially the same function or achieve substantially the same result as the corresponding embodiments described herein may be utilized according to the present invention. Accordingly, the appended claims are intended to include within their scope such processes, machines, manufacture, compositions of matter, means, methods, or steps. Yet, further, all patent applications and issued patents that are referenced herein are incorporated herein by reference.

What is claimed is:

1. A microfluidic device comprising a microchannel structure in which there are one or more inlet ports, one or more outlet ports, and one or more structural units wherein said structural unit comprises:
    (a) a retaining microcavity which is located between one of said one or more inlet ports and one of said one or more outlet ports;
    (b) a mixing unit which is located upstream the retaining microcavity and downstream one of said inlet ports;
    (c) two or more microconduits directly connected to the retaining microcavity and communicating with one of said inlet or outlet ports; wherein one or more of said microconduits comprise anti-wicking means in association with the joint between the retaining microcavity and the microconduit and/or the distance ($d_1$) from the retaining microcavity to an opening to ambient atmosphere and including a microconduit that lacks anti-wicking means and is directly attached to the retaining microcavity, is $\geq 20$ times the largest inner cross-sectional dimension of the microconduit at its joint to the retaining microcavity.

2. The microfluidic device of claim 1, wherein the microconduit comprising anti-wicking means is a liquid flow microconduit and a microconduit lacking anti-wicking means is an air microconduit.

3. The microfluidic of claim 1, wherein at least one of said microconduits has
    one or more length-going edges extending continuously from said retaining microcavity, wherein said anti-wicking means is
    a change in geometric and/or chemical surface characteristics in at least one of said one or more edges.

4. The microfluidic device of claim 3, wherein said anti-wicking means is said change in geometric surface characteristics and is in the form of an indentation.

5. The microfluidic device claim 3, wherein said anti-wicking means is said change in chemical surface characteristics and is in the form of a hydrophobic surface break within the microconduit while the retaining microcavity has hydrophilic inner surfaces.

6. The microfluidic device of claim 3, wherein said change in geometric and/or chemical surface characteristics is extending between two edges delineating an inner wall.

7. The microfluidic device of claim 1, wherein at least one of said microconduits comprise a non-closing valve function essentially at its joint with the retaining microcavity.

8. The microfluidic device of claim 7, wherein said valve function is a hydrophobic surface break at the valve function, and/or a capillary barrier caused by a change in geometric surface characteristics, and/or a curvature in said at least one microconduit comprising the valve function.

9. The microfluidic device of claim 7, wherein said valve function at least partially coincides with the anti-wicking means of said at least one microconduit.

10. The microfluidic device of claim 1, wherein said mixing unit comprises at least two inlet microconduits for said two or more liquid aliquots to be mixed.

11. The microfluidic device of claim 1, wherein the device comprises a plurality of said microchannel structure.

12. The microfluidic device of claim 11, wherein the devise further comprises
    (a) an axis of symmetry coinciding with a spin axis,
    (b) each of said microchannel structures is arranged relative to said axes with a downstream part more remote to said axes than an upstream part, and
    (c) application of centrifugal force by spinning the device about said axes being capable of forcing a liquid aliquot that is present at the same position in each of said microchannel structures to be transported in parallel in the downstream direction within said microchannel structure.

13. A microfluidic device having a microchannel structure in which there are one or more inlet ports, one or more outlet ports, and a structural unit in communication with at least one of said ports, wherein the structural unit is a mixing unit that enables mixing of two aliquots that are miscible with each other, and which said mixing unit comprises: a microcavity with an outlet opening; an inlet arrangement linked to the microcavity, and a mixing microconduit connected to the outlet opening.

14. A microfluidic device having a microchannel structure in which there are one or more inlet ports, one or more outlet ports, and a structural unit in communication with at least one of said ports, wherein the structural unit is a distribution manifold which enables partition of a larger portion of liquid into smaller aliquots which subsequently are introduced in parallel into downstream parts of separate microchannel structures, and which said manifold comprises (a) a continuous microconduit containing an upper part at each end and therebetween alternating lower and upper parts, the number of upper parts is n and the number of lower parts is n−1 where n is an integer $\geq 2$;

(b) a vent to ambient atmosphere and/or anti-wicking means in length-going edges delineating its lower wall (s) in each of the upper parts;

(c) an emptying opening in each of the lower parts which opening in a downstream direction via a connecting microconduit communicates with the remaining substructure of the microchannel structure or with the corresponding substructure of another microchannel structure;

(d) a valve in each of the connecting microconduits;

(e) an inlet port which is connected to the continuous microconduit directly or indirectly at one of the upper parts; and (f) an outlet port which is connected to the continuous microconduit directly or indirectly at an upper part that is not connected to said inlet.

15. The microfluidic device of claim 14, wherein the inlet port is connected to the continuous microconduit directly or indirectly at one of the end parts.

16. A microfluidic device having a microchannel structure in which there are one or more inlet ports, one or more outlet ports, and a structural unit in communication with at least one of said ports, wherein the structural unit is an inlet port which promotes penetration from an inlet opening into the microchannel structure and said inlet port comprises:

a) a microcavity;

b) an inlet opening c) an inlet microconduit located downstream said microcavity and in communication with the interior of the microchannel structure; and d) one, two or more grooves and/or ridges in the inner wall of the microcavity which grooves and/or ridges are directed towards the connection between the microcavity and the inlet microconduit.

17. A microfluidic device comprising a microchannel structure in which there are one or more inlet ports, one or more outlet ports, and a structural unit in communication with at least one of said ports, wherein said structural unit is the integrated volume defining unit that enables volume-definition of an aliquot within the microchannel structure and which said volume defining unit comprises:

a) a volume-defining microcavity;

b) an inlet microconduit which is connected to the microcavity via an inlet opening of the microcavity;

c) an outlet microconduit which is connected to the microcavity via an outlet opening of the microcavity with a valve at the joint between the outlet microconduit and microcavity; and d) an overflow microconduit, which is connected to an overflow opening of the microcavity which overflow opening is at the same level as the joint between the inlet microconduit and the volume defining microcavity, the microcavity being constricted at the overflow opening;

wherein the overflow opening is at a higher level than the outlet opening and the volume being defined as the volume between the valve and the overflow opening.

* * * * *

UNITED STATES PATENT AND TRADEMARK OFFICE
CERTIFICATE OF CORRECTION

PATENT NO. : 6,919,058 B2  
APPLICATION NO. : 10/229676  
DATED : July 19, 2005  
INVENTOR(S) : Per Andersson et al.

It is certified that error appears in the above-identified patent and that said Letters Patent is hereby corrected as shown below:

In the Claims:

At Column 28, Lines 14-37, delete Claim 17.

Signed and Sealed this

Twelfth Day of June, 2007

JON W. DUDAS  
*Director of the United States Patent and Trademark Office*

UNITED STATES PATENT AND TRADEMARK OFFICE
Certificate

Patent No. 6,919,058 B2          Patented: July 19, 2005

On petition requesting issuance of a certificate for correction of inventorship pursuant to 35 U.S.C. 256, it has been found that the above identified patent, through error and without any deceptive intent, improperly sets forth the inventorship.

Accordingly, it is hereby certified that the correct inventorship of this patent is: Per Andersson, Uppsala (SE); Gunnar Ekstrand, Uppsala (SE); Gunnar Thorsén, Stockholm (SE); and Helene Dérand, Taby (SE).

Signed and Sealed this Tenth Day of July 2007.

STEVEN P. GRIFFIN
*Supervisory Patent Examiner*
Art Unit 1731/1723